(12) United States Patent
Kalafut et al.

(10) Patent No.: US 9,421,330 B2
(45) Date of Patent: Aug. 23, 2016

(54) MITIGATION OF CONTRAST-INDUCED NEPHROPATHY

(75) Inventors: John F. Kalafut, Pittsburgh, PA (US); Alan D. Hirschman, Glenshaw, PA (US); David M. Griffiths, Pittsburgh, PA (US); Thomas P. Joyce, Wilkins Township, PA (US); Jerry A. Stokes, Apollo, PA (US); Gerald W. Callan, Cranberry Township, PA (US); Dennis P. Hack, Cheswick, PA (US); Julie Gulick, Murrysville, PA (US); Andreas R. Maihoefer, Cheswick, PA (US); Arthur E. Uber, III, Pittsburgh, PA (US)

(73) Assignee: Bayer HealthCare LLC, Whippany, NJ (US)

( * ) Notice: Subject to any disclaimer, the term of this patent is extended or adjusted under 35 U.S.C. 154(b) by 705 days.

(21) Appl. No.: 12/611,172

(22) Filed: Nov. 3, 2009

(65) Prior Publication Data
US 2010/0114064 A1 May 6, 2010

Related U.S. Application Data

(60) Provisional application No. 61/110,640, filed on Nov. 3, 2008.

(51) Int. Cl.
*A61M 5/172* (2006.01)
*G06F 19/00* (2011.01)
(Continued)

(52) U.S. Cl.
CPC .............. *A61M 5/1723* (2013.01); *A61B 5/411* (2013.01); *A61B 6/481* (2013.01); *A61B 6/482* (2013.01); *A61B 6/504* (2013.01); *A61M 5/142* (2013.01);
(Continued)

(58) Field of Classification Search
CPC .... A61M 5/007; A61M 5/1723; A61B 5/411; A61B 6/481; G06F 19/3431; G06F 19/3468; G06F 19/34; G06F 19/3406; G06F 19/3418; G06F 19/3456
USPC .............. 604/65–67, 131, 503; 600/431–433
See application file for complete search history.

(56) References Cited

U.S. PATENT DOCUMENTS 3,349,713 A    10/1967  Fassbender
3,520,295 A     7/1970  Kelly
(Continued)

FOREIGN PATENT DOCUMENTS

CA    2045070 A1    2/1992
CA    2077712 A1   12/1993
(Continued)

OTHER PUBLICATIONS

Sung, et al. "Urine Attenuation Ratio: A Mew CT Indicator or Renal Artery Stenosis", AJR 2006; 187:532-540.
(Continued)

*Primary Examiner* — Bhisma Mehta
*Assistant Examiner* — Larry R Wilson
(74) *Attorney, Agent, or Firm* — James R. Stevenson; Gregory L. Bradley; Bryan Clark

(57) ABSTRACT

A system which includes a pressurizing mechanism to pressurize a fluid including a contrast enhancement agent for delivery to a patient and a control system in operative connection with the pressurizing mechanism. The control system includes a system to adjust control of fluid injection based upon a measurement of renal function of the patient.

22 Claims, 12 Drawing Sheets

(51) Int. Cl.
  *A61B 5/00* (2006.01)
  *A61B 6/00* (2006.01)
  *A61M 5/142* (2006.01)
  *A61B 5/055* (2006.01)
  *A61B 5/20* (2006.01)
  *A61M 5/00* (2006.01)

(52) U.S. Cl.
  CPC ........ *G06F 19/3431* (2013.01); *G06F 19/3468* (2013.01); *A61B 5/055* (2013.01); *A61B 5/201* (2013.01); *A61M 5/007* (2013.01); *A61M 2210/1082* (2013.01)

(56) References Cited

U.S. PATENT DOCUMENTS

| | | |
|---|---|---|
| 3,523,523 A | 8/1970 | Heinrich et al. |
| 3,623,474 A | 11/1971 | Heilman et al. |
| 3,701,345 A | 10/1972 | Heilman et al. |
| 3,755,655 A | 8/1973 | Senecal |
| 3,793,600 A | 2/1974 | Grosbard |
| 3,812,843 A | 5/1974 | Wootten et al. |
| 3,817,843 A | 6/1974 | Barrett |
| 3,839,708 A | 10/1974 | Bredesen et al. |
| 3,888,239 A | 6/1975 | Rubinstein |
| 3,895,220 A | 7/1975 | Nelson et al. |
| 3,898,983 A | 8/1975 | Elam |
| 3,927,955 A | 12/1975 | Spinosa et al. |
| 3,941,126 A | 3/1976 | Dietrich et al. |
| 3,958,103 A | 5/1976 | Oka et al. |
| 3,968,195 A | 7/1976 | Bishop |
| 3,995,381 A | 12/1976 | Manfred et al. |
| 4,001,549 A | 1/1977 | Corwin |
| 4,006,736 A | 2/1977 | Kranys et al. |
| 4,038,981 A | 8/1977 | LeFevre et al. |
| 4,044,757 A | 8/1977 | McWhorter et al. |
| 4,090,502 A | 5/1978 | Tajika |
| 4,135,247 A | 1/1979 | Gordon et al. |
| 4,151,845 A | 5/1979 | Clemens |
| 4,187,057 A | 2/1980 | Xanthopoulos |
| 4,191,183 A | 3/1980 | Mendelson |
| 4,199,000 A | 4/1980 | Edstrom |
| 4,207,871 A | 6/1980 | Jenkins |
| 4,223,675 A | 9/1980 | Williams |
| 4,262,824 A | 4/1981 | Hrynewycz |
| 4,263,916 A | 4/1981 | Brooks et al. |
| 4,280,494 A | 7/1981 | Cosgrove, Jr. et al. |
| 4,284,073 A | 8/1981 | Krause et al. |
| 4,315,247 A | 2/1982 | Germanton |
| 4,319,568 A | 3/1982 | Tregoning |
| 4,340,153 A | 7/1982 | Spivey |
| 4,341,153 A | 7/1982 | Bowser |
| 4,392,847 A | 7/1983 | Whitney et al. |
| 4,392,849 A | 7/1983 | Petre et al. |
| 4,396,385 A | 8/1983 | Kelly et al. |
| 4,402,310 A | 9/1983 | Kimura |
| 4,409,966 A | 10/1983 | Lambrecht et al. |
| 4,434,820 A | 3/1984 | Glass |
| 4,434,822 A | 3/1984 | Bellamy et al. |
| 4,444,198 A | 4/1984 | Petre |
| 4,447,230 A | 5/1984 | Gula et al. |
| 4,448,200 A | 5/1984 | Brooks et al. |
| 4,474,476 A | 10/1984 | Thomsen |
| 4,477,923 A | 10/1984 | Baumann et al. |
| 4,479,760 A | 10/1984 | Bilstad et al. |
| 4,479,761 A | 10/1984 | Bilstad et al. |
| 4,479,762 A | 10/1984 | Bilstad et al. |
| 4,504,908 A | 3/1985 | Riederer et al. |
| 4,509,526 A | 4/1985 | Barnes et al. |
| 4,512,764 A | 4/1985 | Wunsch |
| 4,542,459 A | 9/1985 | Riederer |
| 4,544,949 A | 10/1985 | Kurihara |
| 4,551,133 A | 11/1985 | Zegers de Beyl et al. |
| 4,552,130 A | 11/1985 | Kinoshita |
| 4,559,036 A | 12/1985 | Wunsch |
| 4,563,175 A | 1/1986 | LaFond |
| 4,578,802 A | 3/1986 | Itoh |
| 4,585,009 A | 4/1986 | Barker et al. |
| 4,585,941 A | 4/1986 | Bergner |
| 4,610,670 A | 9/1986 | Spencer |
| 4,610,790 A | 9/1986 | Reti et al. |
| 4,611,340 A | 9/1986 | Okazaki |
| 4,612,572 A | 9/1986 | Komatsu et al. |
| 4,625,494 A | 12/1986 | Iwatschenko et al. |
| 4,626,144 A | 12/1986 | Berner |
| 4,633,307 A | 12/1986 | Honda |
| 4,634,426 A | 1/1987 | Kamen |
| 4,636,144 A | 1/1987 | Abe et al. |
| 4,655,197 A | 4/1987 | Atkinson |
| 4,662,906 A | 5/1987 | Matkovich et al. |
| 4,672,651 A | 6/1987 | Horiba et al. |
| 4,676,776 A | 6/1987 | Howson |
| 4,682,170 A | 7/1987 | Kubota et al. |
| 4,689,670 A | 8/1987 | Okazaki |
| 4,710,166 A | 12/1987 | Thompson et al. |
| 4,723,261 A | 2/1988 | Janssen et al. |
| 4,750,643 A | 6/1988 | Wortrich |
| 4,754,786 A | 7/1988 | Roberts |
| 4,781,687 A | 11/1988 | Wall |
| 4,783,273 A | 11/1988 | Knutsson et al. |
| 4,789,014 A | 12/1988 | DiGianfilippo et al. |
| 4,793,357 A | 12/1988 | Lindstrom |
| 4,795,429 A | 1/1989 | Feldstein |
| 4,798,590 A | 1/1989 | O'Leary et al. |
| 4,804,454 A | 2/1989 | Asakura et al. |
| 4,823,833 A | 4/1989 | Hogan et al. |
| 4,835,521 A | 5/1989 | Andrejasich et al. |
| 4,836,187 A | 6/1989 | Iwakoshi et al. |
| 4,838,856 A | 6/1989 | Mulreany et al. |
| 4,840,620 A | 6/1989 | Kobayashi et al. |
| 4,844,052 A | 7/1989 | Iwakoshi et al. |
| 4,853,521 A | 8/1989 | Claeys et al. |
| 4,854,301 A | 8/1989 | Nakajima |
| 4,854,324 A | 8/1989 | Hirschman et al. |
| 4,857,056 A | 8/1989 | Talonn |
| 4,874,359 A | 10/1989 | White et al. |
| 4,879,880 A | 11/1989 | Harrison |
| 4,880,014 A | 11/1989 | Zarowitz et al. |
| 4,887,208 A | 12/1989 | Schneider et al. |
| 4,887,554 A | 12/1989 | Whitford |
| 4,901,731 A | 2/1990 | Millar |
| 4,903,705 A | 2/1990 | Imamura et al. |
| 4,913,154 A | 4/1990 | Ermert et al. |
| 4,922,916 A | 5/1990 | Ermert et al. |
| 4,925,444 A | 5/1990 | Orkin et al. |
| 4,929,818 A | 5/1990 | Bradbury et al. |
| 4,935,005 A | 6/1990 | Haines |
| 4,936,832 A | 6/1990 | Vaillancourt |
| 4,943,279 A | 7/1990 | Samiotes et al. |
| 4,943,779 A | 7/1990 | Pedersen et al. |
| 4,943,987 A | 7/1990 | Asahina et al. |
| 4,946,256 A | 8/1990 | Woodruff |
| 4,946,439 A | 8/1990 | Eggers |
| 4,947,412 A | 8/1990 | Mattson |
| 4,950,245 A | 8/1990 | Brown et al. |
| 4,954,129 A | 9/1990 | Giuliani et al. |
| 4,965,726 A | 10/1990 | Heuscher et al. |
| 4,966,579 A | 10/1990 | Polaschegg |
| 4,976,687 A | 12/1990 | Martin |
| 4,978,335 A | 12/1990 | Arthur, III |
| 4,981,467 A | 1/1991 | Bobo, Jr. et al. |
| 4,995,064 A | 2/1991 | Wilson et al. |
| 5,002,055 A | 3/1991 | Merki et al. |
| 5,004,472 A | 4/1991 | Wallace |
| 5,009,654 A | 4/1991 | Minshall et al. |
| 5,010,473 A | 4/1991 | Jacobs |
| 5,013,173 A | 5/1991 | Shiraishi |
| 5,018,173 A | 5/1991 | Komai et al. |
| 5,032,112 A | 7/1991 | Fairchild et al. |
| 5,034,987 A | 7/1991 | Fujimoto et al. |
| 5,040,537 A | 8/1991 | Katakura |
| 5,053,002 A | 10/1991 | Barlow |
| 5,054,044 A | 10/1991 | Audon et al. |
| 5,056,568 A | 10/1991 | DiGianfilippo et al. |

(56) References Cited

U.S. PATENT DOCUMENTS

| | | |
|---|---|---|
| 5,059,173 A | 10/1991 | Sacco |
| 5,061,243 A | 10/1991 | Winchell et al. |
| 5,069,662 A | 12/1991 | Bodden |
| 5,078,683 A | 1/1992 | Sancoff et al. |
| 5,088,981 A | 2/1992 | Howson et al. |
| 5,100,380 A | 3/1992 | Epstein et al. |
| 5,104,374 A | 4/1992 | Bishko et al. |
| 5,104,387 A | 4/1992 | Pokorney et al. |
| 5,108,365 A | 4/1992 | Woods, Jr. |
| 5,111,492 A | 5/1992 | Klausz |
| 5,113,905 A | 5/1992 | Pruitt et al. |
| 5,123,056 A | 6/1992 | Wilson |
| 5,123,121 A | 6/1992 | Broersma |
| 5,125,018 A | 6/1992 | Asahina |
| 5,128,121 A | 7/1992 | Berg et al. |
| 5,133,336 A | 7/1992 | Savitt et al. |
| 5,135,000 A | 8/1992 | Akselrod et al. |
| 5,150,292 A | 9/1992 | Hoffmann et al. |
| 5,166,961 A | 11/1992 | Brunnett et al. |
| 5,180,895 A | 1/1993 | Briggs et al. |
| 5,180,896 A | 1/1993 | Gibby et al. |
| 5,190,744 A | 3/1993 | Rocklage et al. |
| 5,191,878 A | 3/1993 | Iida et al. |
| 5,196,007 A | 3/1993 | Ellman et al. |
| 5,199,604 A | 4/1993 | Palmer et al. |
| 5,207,642 A | 5/1993 | Orkin et al. |
| 5,215,095 A | 6/1993 | Macvicar et al. |
| 5,228,070 A | 7/1993 | Mattson |
| 5,230,614 A | 7/1993 | Zanger et al. |
| 5,242,390 A | 9/1993 | Goldrath |
| 5,249,122 A | 9/1993 | Stritzke |
| 5,249,579 A | 10/1993 | Hobbs et al. |
| 5,262,946 A | 11/1993 | Heuscher |
| 5,267,174 A | 11/1993 | Kaufman et al. |
| 5,269,756 A | 12/1993 | Dryden |
| 5,273,537 A | 12/1993 | Haskvitz et al. |
| 5,274,218 A | 12/1993 | Urata et al. |
| 5,276,174 A | 1/1994 | Plotkin et al. |
| 5,276,614 A | 1/1994 | Heuscher |
| 5,286,252 A | 2/1994 | Tuttle et al. |
| 5,287,273 A | 2/1994 | Kupfer et al. |
| 5,300,031 A | 4/1994 | Neer et al. |
| 5,301,656 A | 4/1994 | Negoro et al. |
| 5,301,672 A | 4/1994 | Kalender |
| 5,304,126 A | 4/1994 | Epstein et al. |
| 5,310,997 A | 5/1994 | Roach et al. |
| 5,311,568 A | 5/1994 | McKee, Jr. et al. |
| 5,313,992 A | 5/1994 | Grabenkort |
| 5,317,506 A | 5/1994 | Coutre et al. |
| 5,328,463 A | 7/1994 | Barton et al. |
| 5,329,459 A | 7/1994 | Kaufman et al. |
| 5,339,799 A | 8/1994 | Kami et al. |
| 5,349,625 A | 9/1994 | Born et al. |
| 5,349,635 A | 9/1994 | Scott |
| 5,352,979 A | 10/1994 | Conturo |
| 5,354,273 A | 10/1994 | Hagen |
| 5,361,761 A | 11/1994 | Van Lysel et al. |
| 5,362,948 A | 11/1994 | Morimoto |
| 5,368,562 A | 11/1994 | Blomquist et al. |
| 5,368,567 A | 11/1994 | Lee |
| 5,368,570 A | 11/1994 | Thompson et al. |
| 5,373,231 A | 12/1994 | Boll et al. |
| 5,376,070 A | 12/1994 | Purvis et al. |
| 5,378,231 A | 1/1995 | Johnson et al. |
| 5,382,232 A | 1/1995 | Hague et al. |
| 5,383,058 A | 1/1995 | Yonezawa |
| 5,383,231 A | 1/1995 | Yamagishi |
| 5,383,858 A | 1/1995 | Reilly et al. |
| 5,385,540 A | 1/1995 | Abbott et al. |
| 5,388,139 A | 2/1995 | Beland |
| 5,392,849 A | 2/1995 | Matsunaga et al. |
| 5,400,792 A | 3/1995 | Hoebel et al. |
| 5,417,213 A | 5/1995 | Prince |
| 5,417,219 A | 5/1995 | Takamizawa et al. |
| 5,431,627 A | 7/1995 | Pastrone et al. |
| 5,433,704 A | 7/1995 | Ross et al. |
| 5,445,621 A | 8/1995 | Poli et al. |
| 5,450,847 A | 9/1995 | Kampfe et al. |
| 5,453,639 A | 9/1995 | Cronin et al. |
| 5,456,255 A | 10/1995 | Abe et al. |
| 5,458,128 A | 10/1995 | Polanyi et al. |
| 5,459,769 A | 10/1995 | Brown |
| 5,460,609 A | 10/1995 | O'Donnell |
| 5,464,391 A | 11/1995 | DeVale |
| 5,468,240 A | 11/1995 | Gentelia et al. |
| 5,469,769 A | 11/1995 | Sawada et al. |
| 5,469,849 A | 11/1995 | Sasaki et al. |
| 5,472,403 A | 12/1995 | Cornacchia et al. |
| 5,474,683 A | 12/1995 | Bryant et al. |
| 5,485,831 A | 1/1996 | Holdsworth et al. |
| 5,489,265 A | 2/1996 | Montalvo et al. |
| 5,494,036 A | 2/1996 | Uber, III et al. |
| 5,494,822 A | 2/1996 | Sadri |
| 5,496,273 A | 3/1996 | Pastrone et al. |
| 5,507,412 A | 4/1996 | Ebert et al. |
| 5,515,851 A | 5/1996 | Goldstein |
| 5,522,798 A | 6/1996 | Johnson et al. |
| 5,531,679 A | 7/1996 | Schulman et al. |
| 5,531,697 A | 7/1996 | Olsen et al. |
| 5,533,978 A | 7/1996 | Teirstein |
| 5,544,215 A | 8/1996 | Shroy, Jr. et al. |
| 5,547,470 A | 8/1996 | Johnson et al. |
| 5,552,130 A | 9/1996 | Kraus et al. |
| 5,553,619 A | 9/1996 | Prince |
| 5,560,317 A | 10/1996 | Bunyan et al. |
| 5,566,092 A | 10/1996 | Wang et al. |
| 5,569,181 A | 10/1996 | Heilman et al. |
| 5,569,208 A | 10/1996 | Woelpper et al. |
| 5,573,515 A | 11/1996 | Wilson et al. |
| 5,579,767 A | 12/1996 | Prince |
| 5,583,902 A | 12/1996 | Bae |
| 5,590,654 A | 1/1997 | Prince |
| 5,592,940 A | 1/1997 | Kampfe et al. |
| 5,601,086 A | 2/1997 | Pretlow, III et al. |
| 5,611,344 A | 3/1997 | Bernstein et al. |
| 5,616,124 A | 4/1997 | Hague et al. |
| 5,681,285 A | 10/1997 | Ford et al. |
| 5,687,208 A | 11/1997 | Bae et al. |
| 5,687,708 A | 11/1997 | Farnsworth et al. |
| 5,713,358 A | 2/1998 | Mistretta et al. |
| 5,724,976 A | 3/1998 | Mine et al. |
| 5,739,508 A | 4/1998 | Uber, III |
| 5,743,266 A | 4/1998 | Levene et al. |
| 5,768,405 A | 6/1998 | Makram-Ebeid |
| 5,796,862 A | 8/1998 | Pawlicki et al. |
| 5,799,649 A | 9/1998 | Prince |
| 5,800,397 A | 9/1998 | Wilson et al. |
| 5,806,519 A | 9/1998 | Evans, III et al. |
| 5,808,203 A | 9/1998 | Nolan, Jr. et al. |
| 5,827,219 A | 10/1998 | Uber, III et al. |
| 5,827,504 A | 10/1998 | Yan et al. |
| 5,840,026 A | 11/1998 | Uber, III et al. |
| 5,843,037 A | 12/1998 | Uber, III |
| 5,846,517 A | 12/1998 | Unger |
| 5,865,744 A | 2/1999 | Lemelson |
| 5,881,124 A | 3/1999 | Giger et al. |
| 5,882,343 A | 3/1999 | Wilson et al. |
| 5,885,216 A | 3/1999 | Evans, III et al. |
| 5,902,054 A | 5/1999 | Coudray |
| 5,903,454 A * | 5/1999 | Hoffberg et al. ............ 700/83 |
| 5,916,165 A | 6/1999 | Duchon et al. |
| 5,920,054 A | 7/1999 | Uber, III |
| 5,987,347 A | 11/1999 | Khoury et al. |
| 5,988,587 A | 11/1999 | Duchon et al. |
| 6,046,225 A | 4/2000 | Maddock |
| 6,055,985 A | 5/2000 | Bae et al. |
| 6,056,902 A | 5/2000 | Hettinga |
| 6,063,052 A | 5/2000 | Uber, III et al. |
| 6,073,042 A | 6/2000 | Simonetti |
| 6,099,502 A | 8/2000 | Duchon et al. |
| 6,149,627 A | 11/2000 | Uber, III |
| 6,186,146 B1 | 2/2001 | Glickman |
| 6,201,889 B1 | 3/2001 | Vannah |
| 6,221,045 B1 | 4/2001 | Duchon et al. |

(56) References Cited

U.S. PATENT DOCUMENTS

| | | |
|---|---|---|
| 6,236,706 B1 | 5/2001 | Hsieh |
| 6,248,093 B1 | 6/2001 | Moberg |
| 6,306,117 B1 | 10/2001 | Uber, III |
| 6,313,131 B1 | 11/2001 | Lawyer |
| 6,317,623 B1 | 11/2001 | Griffiths et al. |
| 6,344,030 B1 | 2/2002 | Duchon et al. |
| 6,381,486 B1 | 4/2002 | Mistretta et al. |
| 6,385,483 B1 | 5/2002 | Uber, III et al. |
| 6,387,098 B1 | 5/2002 | Cole et al. |
| 6,397,093 B1 | 5/2002 | Aldrich |
| 6,397,097 B1 | 5/2002 | Requardt |
| 6,397,098 B1 | 5/2002 | Uber, III et al. |
| 6,402,697 B1 | 6/2002 | Calkins et al. |
| 6,423,719 B1 | 7/2002 | Lawyer |
| 6,442,418 B1 | 8/2002 | Evans, III et al. |
| 6,470,889 B1 | 10/2002 | Bae et al. |
| 6,471,674 B1 | 10/2002 | Emig et al. |
| 6,478,735 B1 | 11/2002 | Pope et al. |
| 6,503,226 B1 | 1/2003 | Martinell Gisper-Sauch et al. |
| 6,520,930 B2 | 2/2003 | Critchlow et al. |
| 6,527,718 B1 | 3/2003 | Connor et al. |
| 6,554,819 B2 | 4/2003 | Reich |
| 6,556,695 B1 | 4/2003 | Packer et al. |
| 6,572,851 B2 | 6/2003 | Muramatsu et al. |
| 6,574,496 B1 | 6/2003 | Golman et al. |
| 6,575,930 B1 | 6/2003 | Trombley, III et al. |
| 6,597,938 B2 | 7/2003 | Liu |
| 6,626,862 B1 | 9/2003 | Duchon et al. |
| 6,635,030 B1 | 10/2003 | Bae et al. |
| 6,643,537 B1 | 11/2003 | Zatezalo et al. |
| 6,652,489 B2 | 11/2003 | Trocki et al. |
| 6,656,157 B1 | 12/2003 | Duchon et al. |
| 6,673,033 B1 | 1/2004 | Sciulli et al. |
| 6,685,733 B1 | 2/2004 | Dae et al. |
| 6,691,047 B1 | 2/2004 | Fredericks |
| 6,699,219 B2 | 3/2004 | Emig et al. |
| 6,731,971 B2 | 5/2004 | Evans, III et al. |
| 6,754,521 B2 | 6/2004 | Prince |
| 6,775,764 B1 | 8/2004 | Batcher |
| 6,776,764 B2 | 8/2004 | Pinsky |
| 6,866,653 B2 | 3/2005 | Bae |
| 6,866,654 B2 | 3/2005 | Callan et al. |
| 6,876,720 B2 | 4/2005 | Tsuyuki |
| 6,879,853 B2 | 4/2005 | Meaney et al. |
| 6,887,214 B1 | 5/2005 | Levin et al. |
| 6,889,074 B2 | 5/2005 | Uber, III et al. |
| 6,901,283 B2 | 5/2005 | Evans, III et al. |
| 6,970,735 B2 | 11/2005 | Uber, III et al. |
| 6,972,001 B2 | 12/2005 | Emig et al. |
| 6,983,590 B2 | 1/2006 | Roelle et al. |
| 6,994,700 B2 | 2/2006 | Elkins et al. |
| 7,094,216 B2 | 8/2006 | Trombley, III et al. |
| 7,104,981 B2 | 9/2006 | Elkins et al. |
| 7,108,981 B2 | 9/2006 | Aoki et al. |
| 7,163,520 B2 | 1/2007 | Bernard et al. |
| 7,266,227 B2 | 9/2007 | Pedain et al. |
| 7,267,666 B1 | 9/2007 | Duchon et al. |
| 7,267,667 B2 | 9/2007 | Houde et al. |
| 7,292,720 B2 | 11/2007 | Horger et al. |
| 7,313,431 B2 | 12/2007 | Uber, III et al. |
| 7,326,186 B2 | 2/2008 | Trombley, III et al. |
| 7,363,072 B2 | 4/2008 | Movahed |
| 8,428,694 B2 | 4/2013 | Kalafut et al. |
| 8,486,017 B2 | 7/2013 | Masuda et al. |
| 2001/0027265 A1 | 10/2001 | Prince |
| 2001/0056233 A1 | 12/2001 | Uber et al. |
| 2002/0010551 A1 | 1/2002 | Wang et al. |
| 2002/0026148 A1 | 2/2002 | Uber |
| 2002/0091349 A1 | 7/2002 | Reich |
| 2002/0099254 A1 | 7/2002 | Movahed |
| 2002/0123702 A1 | 9/2002 | Cho |
| 2002/0151854 A1 | 10/2002 | Duchon et al. |
| 2002/0165445 A1 | 11/2002 | Uber et al. |
| 2003/0015078 A1 | 1/2003 | Taylor |
| 2003/0036694 A1 | 2/2003 | Liu |
| 2003/0050556 A1 | 3/2003 | Uber et al. |
| 2003/0120171 A1 | 6/2003 | Diamantopoulos et al. |
| 2003/0135111 A1 | 7/2003 | Meaney et al. |
| 2003/0195462 A1 | 10/2003 | Mann et al. |
| 2003/0212364 A1 | 11/2003 | Mann et al. |
| 2003/0216683 A1 | 11/2003 | Shekalim |
| 2004/0008028 A1 | 1/2004 | Horger et al. |
| 2004/0010229 A1 | 1/2004 | Houde et al. |
| 2004/0011740 A1 | 1/2004 | Bernard et al. |
| 2004/0015078 A1 | 1/2004 | Evans et al. |
| 2004/0025452 A1 | 2/2004 | McLean |
| 2004/0044302 A1 | 3/2004 | Bernard et al. |
| 2004/0064040 A1 | 4/2004 | Masuda et al. |
| 2004/0064041 A1 | 4/2004 | Lazzaro et al. |
| 2004/0097806 A1 | 5/2004 | Hunter et al. |
| 2004/0097875 A1 | 5/2004 | Bae |
| 2004/0162484 A1 | 8/2004 | Nemoto |
| 2004/0163655 A1 | 8/2004 | Gelfand et al. |
| 2004/0167415 A1 | 8/2004 | Gelfand et al. |
| 2004/0215144 A1 | 10/2004 | Duchon et al. |
| 2005/0004517 A1 | 1/2005 | Courtney et al. |
| 2005/0053551 A1 | 3/2005 | Badiola |
| 2005/0112178 A1 | 5/2005 | Stern |
| 2005/0256441 A1 | 11/2005 | Lotan et al. |
| 2006/0013772 A1 | 1/2006 | LeWinter et al. |
| 2006/0052764 A1 | 3/2006 | Gelfand et al. |
| 2006/0074294 A1* | 4/2006 | Williams et al. ............... 600/420 |
| 2006/0079843 A1 | 4/2006 | Brooks et al. |
| 2006/0096388 A1 | 5/2006 | Gysling et al. |
| 2006/0184099 A1* | 8/2006 | Hong ............................ 604/43 |
| 2006/0211989 A1 | 9/2006 | Rhinehart et al. |
| 2006/0235353 A1* | 10/2006 | Gelfand et al. ................ 604/66 |
| 2006/0235474 A1 | 10/2006 | Demarais |
| 2006/0239918 A1 | 10/2006 | Klotz et al. |
| 2006/0253064 A1 | 11/2006 | Gelfand et al. |
| 2006/0253353 A1 | 11/2006 | Weisberger |
| 2006/0270971 A1 | 11/2006 | Gelfand et al. |
| 2006/0271111 A1 | 11/2006 | Demarais et al. |
| 2007/0016016 A1 | 1/2007 | Haras et al. |
| 2007/0066892 A1 | 3/2007 | Haras et al. |
| 2007/0078330 A1* | 4/2007 | Haras et al. ................... 600/407 |
| 2007/0213662 A1 | 9/2007 | Kalafut et al. |
| 2007/0225601 A1 | 9/2007 | Uber et al. |
| 2007/0255135 A1* | 11/2007 | Kalafut et al. ................ 600/431 |
| 2007/0282199 A1 | 12/2007 | Uber et al. |
| 2007/0282263 A1 | 12/2007 | Kalafut et al. |
| 2008/0009717 A1 | 1/2008 | Herrmann et al. |
| 2008/0045834 A1 | 2/2008 | Uber et al. |
| 2008/0046286 A1* | 2/2008 | Halsted ................ G06F 19/322 705/2 |
| 2008/0097197 A1 | 4/2008 | Kalafut et al. |
| 2008/0097339 A1 | 4/2008 | Ranchod et al. |
| 2008/0101678 A1 | 5/2008 | Suliga et al. |
| 2008/0119715 A1 | 5/2008 | Gonzalez Molezzi et al. |
| 2013/0211247 A1 | 8/2013 | Kalafut |

FOREIGN PATENT DOCUMENTS

| | | |
|---|---|---|
| CA | 2234050 A1 | 4/1997 |
| CN | 1343107 | 4/2002 |
| DE | 3726452 | 2/1989 |
| DE | 3726452 A1 | 2/1989 |
| DE | 4121568 A1 | 10/1992 |
| DE | 4426387 | 8/1995 |
| DE | 19702896 A1 | 7/1997 |
| DE | 19647701 A1 | 5/1998 |
| DE | 69530035 T2 | 9/2003 |
| EP | 0121216 A1 | 10/1984 |
| EP | 0129910 A1 | 1/1985 |
| EP | 0189491 | 8/1986 |
| EP | 0189491 A1 | 8/1986 |
| EP | 0192786 A2 | 9/1986 |
| EP | 0245160 A1 | 11/1987 |
| EP | 0337924 A2 | 10/1989 |
| EP | 0343501 A2 | 11/1989 |
| EP | 0364966 A1 | 4/1990 |
| EP | 0365301 A1 | 4/1990 |
| EP | 0372152 A1 | 6/1990 |
| EP | 0378896 A2 | 7/1990 |

(56) References Cited

FOREIGN PATENT DOCUMENTS

| | | | |
|---|---|---|---|
| EP | 0429191 | A2 | 5/1991 |
| EP | 0471455 | A2 | 2/1992 |
| EP | 0475563 | A1 | 3/1992 |
| EP | 0595474 | A2 | 5/1994 |
| EP | 0600448 | A2 | 6/1994 |
| EP | 0619122 | A1 | 10/1994 |
| EP | 0439711 | | 5/1995 |
| EP | 0650738 | A1 | 5/1995 |
| EP | 0650739 | A1 | 5/1995 |
| EP | 0702966 | A2 | 3/1996 |
| EP | 0869738 | A1 | 10/1998 |
| EP | 1262206 | A2 | 12/2002 |
| FR | 2561949 | | 10/1985 |
| FR | 2561949 | A1 | 10/1985 |
| GB | 201800 | A | 8/1923 |
| GB | 2252656 | A | 8/1992 |
| GB | 2328745 | A | 3/1999 |
| JP | 58015842 | A | 1/1983 |
| JP | 60253197 | A | 12/1985 |
| JP | 62216199 | A | 9/1987 |
| JP | 63290547 | A | 11/1988 |
| JP | 1207038 | A | 8/1989 |
| JP | 2224647 | A | 9/1990 |
| JP | 2234747 | A | 9/1990 |
| JP | 3055040 | A | 3/1991 |
| JP | 4115677 | A | 4/1992 |
| JP | 5084296 | A | 4/1993 |
| JP | 7178169 | A | 7/1995 |
| JP | 10211198 | A | 8/1998 |
| JP | 2000506398 | A | 5/2000 |
| JP | 2002-507438 | | 3/2002 |
| JP | 2003-102724 | A | 4/2003 |
| JP | 2003-116843 | | 4/2003 |
| JP | 2003-210456 | | 7/2003 |
| JP | 2003-225234 | | 8/2003 |
| JP | 2004-519304 | | 7/2004 |
| JP | 2004298550 | A | 10/2004 |
| WO | 8001754 | A1 | 9/1980 |
| WO | 8500292 | A1 | 1/1985 |
| WO | 8803815 | A1 | 6/1988 |
| WO | 9114232 | A1 | 9/1991 |
| WO | 9114233 | A1 | 9/1991 |
| WO | 9315658 | A1 | 8/1993 |
| WO | 9325141 | A1 | 12/1993 |
| WO | 9415664 | A1 | 7/1994 |
| WO | 9632975 | A1 | 10/1996 |
| WO | 9712550 | A1 | 4/1997 |
| WO | 9820919 | A1 | 5/1998 |
| WO | 9924095 | A2 | 5/1999 |
| WO | 0061216 | A1 | 10/2000 |
| WO | 0064353 | A2 | 11/2000 |
| WO | 03015633 | A1 | 2/2003 |
| WO | 2004012787 | A2 | 2/2004 |
| WO | 2005004038 | A1 | 1/2005 |
| WO | 2005016165 | | 2/2005 |
| WO | 2006042093 | | 4/2006 |
| WO | 2006055813 | | 5/2006 |
| WO | WO2006/055813 | | 5/2006 |
| WO | WO2006/058280 | | 6/2006 |
| WO | 2007143682 | | 12/2007 |
| WO | WO2007/143682 | | 12/2007 |
| WO | 2008011401 | A2 | 1/2008 |
| WO | 2008082937 | | 7/2008 |
| WO | 2008085421 | | 7/2008 |
| WO | WO2008/082937 | | 7/2008 |
| WO | WO2008/085421 | | 7/2008 |
| WO | 2009012023 | | 1/2009 |
| WO | WO2009/012023 | | 1/2009 |

OTHER PUBLICATIONS

Stevens, et al. "A Prospective Randomized Trial of Prevention Measures in Patients at High Risk for Contrast Nephropathy", J of the ACC. vol. 33. No. 2, 1999. pp. 403-411.

Hackstein, et al. "Glomerular Filtration Rate Measured by Using Triphasic Helical CT with a Two-Point Patlak Plot Technique", Radiology, Jan. 2004; 230(1):221-6.

Bae, et al."Aortic and Hepatic Contrast Medium Enhancement at CT—Part I, Prediction with a Computer Model", Radiology 1998;207:647-655.

Jo, etal. "Renal Toxicity Evaluation and Comparison between Visipaque (Iodixanol) and Dexabrix (Ioxaglate) in patients with renal insufficiency undergoing coronary angiography". J of the ACC. V48, No. 5, 2006. pp. 924-930.

S.Goldfarb. "Contrast-induced nephropathy: Risk factors, pathophysiology, and prevention". Applied Radiology (online supplement). Aug. 2005. pp. 5-16.

Buckley, et al. Measurement of single kidney function using dynamic contrast-enhanced MRI: comparison of two models in human subjects. J Magn Reson Imaging. Nov. 2006;24(5):1117-23.

McCullough, P.A., et al., Contrast-Induced Nephropathy (CIN) Consensus Working Panel: Executive Summary. Rev Cardiovasc Med, 2006. 7(4): p. 177-97.

Renalguard, PLC Medical Systems, Inc. News Release. (May 12, 2008).

EZ Chem Brochure, E-Z-EM, Inc. (Jul. 2007).

iSTAT 1 System Manual, Abbott Laboratories (Rev. Aug. 14, 2006).

Non-Final Office Action mailed Dec. 12, 2014, in U.S. Appl. No. 13/186,983.

European Search Report and Opinion mailed on Nov. 21, 2013 from EP No. 13004902.6.

Non-Final Office Action mailed Apr. 23, 2014, in U.S. Appl. No. 12/519,040, John F. Kalafut et al., filed Dec. 29, 2006.

Garrett, J. S., et al., "Measurement of cardiac output by cine computed tomography," The American Journal of Cardiology, vol. 56, Issue 10, pp. 657-661, 1985.

Gembicki, F.W., "Vector Optimization for Control with Performance and Parameter Sensitivity Indices," PhD Thesis, Case Western Reserve University, 1974.

Gentilini A., et al. "A new paradigm for the closed-loop intraoperative administration of analgesics in humans", IEEE Transactions on Biomedical Engineering, vol. 49, Issue 4, pp. 289-299, 2002.

Gerlowski L.E. and Jain R.K., "Physiologically Based Pharmacokinetic Modeling: Principles and Applications," Journal of Pharmaceutical Sciences, vol. 72, pp. 1104-1125, Oct. 1983.

Goss, J. E., et al., "Power injection of contrast media during percutaneous transluminal coronary artery angioplasty," Catheterization and Cardiovascular Diagnosis, vol. 16, pp. 195-198 1989.

Grant, S.C.D. et al., "Reduction of Radiation Exposure to the Cardiologist during Coronary Angiography by the Use of a Remotely Controlled Mechanical Pump for Injection of Contrast Medium," Catheterization and Cardiovascular Diagnosis, vol. 25, Issue 2, pp. 107-109, Feb. 1992.

Guyton, A.C., "Circulatory Physiology: cardiac output and regulation," Saunders, Philadelphia, pp. 173, ISBN: 07216436004, 1985.

Hansen, P.C, Regularization tools: a MATLAB package for analysis and solution of discrete ill-posed problems, Numerical Algorithms, vol. 6, Issue 1, pp. 35, 1994.

Hansen, P.C., "The truncated SVD as a method for regularization," BIT Numerical Mathematics, vol. 27, Issue 4, pp. 534-55, 1987.

Hansen, P.C., et al., "An adaptive pruning algorithm for the discrete L-curve criterion," Journal of Computational and Applied Mathematics, vol. 198, Issue 2, pp. 9, 2007.

Harris P., H. D. "The Human Pulmonary Circulation," Edinburgh, Churchill Livingstone, (Appendix I), 1986.

Hayes, M.H., "Statistical Digital Signal Processing and Modeling," New York, New York: Wiley and Sons, pp. 154-177, 1996.

Heiken, J.P. et al., "Dynamic Contrast-Enhanced CT of the Liver: Comparison of Contrast Medium Injection Rates and Uniphasic and Biphasic Injection Protocols," Radiology, vol. 187, No. 2, May 1993, pp. 327-331.

International Preliminary Report on Patentability, International Search Report, and Written Opinion for International Patent Application No. PCT/US00/10842 issued May 22, 2001.

International Preliminary Report on Patentability International Search Report, and Written Opinion for International Patent Application No. PCT/US2007/026194 issued Jun. 30, 2009.

(56) References Cited

OTHER PUBLICATIONS

Non-Final Office Action mailed Jul. 15, 2014 in related U.S. Appl. No. 11/691,823.
Non-Final Office Action mailed Jul. 14, 2014 in related U.S. Appl. No. 12/519,213.
Sablayrolles, J-L, "Cardiac CT: Experience from Daily Practice," Advance CT, A GE Healthcare Publication, Aug. 2004.
Non-Final Office Action mailed Dec. 12, 2008, in U.S. Appl. No. 11/691,823, John F. Kalafut et al., filed Mar. 27, 2007.
Rosen, B.R. et al., "Perfusion Imaging with NMR Contrast Agents," Magentic Resonance in Medicine, vol. 14, No. 2, pp. 249-265, May 1, 1990.
PHYSBE a classic model of the human circulatory system available from The Math Works, Inc. of Natick, Massachusetts, accessed at www.mathworks.com/products/demos/simulink/physbe, May 31, 2005, pp. 11.
Østergaard, L., et al., "High resolution measurement of cerebral blood flow using intravascular tracer bolus passages. Part 1: Mathematical approach and statistical analysis," Magnetic Resonance in Medicine, vol. 36, Issue 5, pp. 715-725, 1996.
Østergaard, L., et al., "High resolution measurement of cerebral blood flow using intravascular tracer bolus passages. Part II: Experimental comparison and preliminary results," Magn Reson Med, vol. 36, Issue 5, pp. 726-736, 1996.
Non-Final Office Action mailed Feb. 15, 2012, in U.S. Appl. No. 12/519,040, John F. Kalafut, filed Jun. 12, 2009.
Parker, K.J. and Tuthill T.A., "A Particulate Contrast Agent With Potential for Ultrasound Imaging of Liver," Ultrasound in Medicine & Biology vol. 13, Issue 9, pp. 555-566, Sep. 1987.
Non-Final office Action mailed Mar. 12, 2013, in U.S. Appl. No. 13/655,525, John F. Kalafut et al., filed Oct. 19, 2012.
Non-Final Office Action mailed Nov. 5, 2012, in U.S. Appl. No. 13/186,983, John F. Kalafut et al., filed Jul. 20, 2011.
Non-Final Office Action mailed Oct. 18, 2012, in U.S. Appl. No. 12/519,213, John F. Kalafut et al., filed Jun. 15, 2009.
Supplementary European Search Report mailed Apr. 15, 2011 in European Patent Application No. 07867951.1.
Supplementary European Search Report mailed Aug. 19, 2010 in European Patent Application No. 05852259.0.
Supplementary European Search Report mailed Dec. 9, 1998 in European Patent Application No. EP 96936079.0.
Supplementary European Search Report mailed Jul. 23, 2013 in European Patent Application No. 08771789.8.
*Tyco Healthcare Group LP v. MEDRAD. Inc.* Complaint, Case No. 1:06-cv-00763, Nov. 8, 2006.
Wada, D.R. and Ward, D.S., "Open loop control of multiple drug effects in anesthesia", IEEE Transactions on Biomedical Engineering, vol. 42, Issue 7, pp. 666-677, 1995.
Wada, D.R. and Ward, D.S., "The hybrid model: a new pharmacokinetic model for computer-controlled infusion pumps", IEEE Transactions on Biomedical Engineering, vol. 41, Issue 2, pp. 134-142, 1994.
Yamashita, Y. et al., "Abdominal Helical CT: Evaluation of Optimal Doses of Intravenous Contrast Material—A Prospective Randomized Study," Radiology, vol. 216, Issue 3, pp. 718-723, Sep. 1, 2000.
International Preliminary Report on Patentability International Search Report, and Written Opinion for International Patent Application No. PCT/US2008/067982 issued Jan. 19, 2010.
International Preliminary Report on Patentability International Search Report, and Written Opinion for International Patent Application No. PCT/US2009/047168 issued Jan. 5, 2011.
International Preliminary Report on Patentability, International Search Report, and Written Opinion for International Patent Application No. PCT/US2011/041802 issued Dec. 28, 2012.
International Preliminary Report on Patentability, International Search Report, and Wrtitten Opinion for International Patent Application No. PCT/US2005/042891 issued May 30, 2007.
International Preliminary Report on Patentability for International Application No. PCT/EP2005/007791, International Bureau of WIPO, Geneva, Switzerland, issued on May 22, 2007.
International Preliminary Report on Patentability for International Patent Application No. PCT/US2005/041913 issued May 22, 2007.
Non-Final Office Action mailed Apr. 26, 2013, in U.S. Appl. No. 12/519,040, John F. Kalafut, filed Jun. 12, 2009.
International Search Report for International Patent Application No. PCT/US96/15680 mailed Jan. 28, 1997.
Ireland, M.A., et al., "Safety and Convenience of a Mechanical Injector Pump for Coronary Angiography," Catheterization and Cardiovascular Diagnosis, vol. 16, Issue 3, pp. 199-201, 1989.
Jacobs, J.R., "Algorithm for optimal linear model-based control with application to pharmacokinetic model-driven drug delivery," IEEE Transactions on Biomedical Engineering, vol. 37, Issue I, pp. 107-109, 1990.
Koh, T.S., et al., "Assessment of Perfusion by Dynamic Contrast-Enhanced Imaging Using a Deconvolution Approach Based on Regression and Singular Value Decomposition," IEEE Transactions on Medical Imaging, vol. 23, Issue 12, pp. 1532-1542, Dec. 2004.
Korosec, F.R., "Basic Principles of Phase-contrast, Time-of-flight, and Contrast-enhanced MR Angiography", pp. 1-10, 1999.
Korosec, F.R., "Physical Principles of Phase-Contrast, Time-of-Flight, and Contrast-Enhanced MR Angiography," 41st Annual Meeting of American Association of Physicists in Medicine, Jul. 25-29, 1999.
Krause, W., "Application of pharmacokinetics to computed tomography: injection rates and schemes: mono-, bi-, or multiphasic?," Investigative Radiology, vol. 31, Issue 2, pp. 91-100, Feb. 1996.
Krieger, R. A., C02-Power-Assisted Hand-Held Syringe: Better Visualization during Diagnostic and Interventional, vol. 19, Issue 2, pp. 123-128, Feb. 1990.
Liebel-Flarsheim Company, "Angiomat 6000 Digital Injection System—Operator's Manual", Document No. 600950, Rev. 1, 1990.
Mahnken, A. H., et al., "Determination of cardiac output with multislice spiral computed tomography: a validation study," Investigative Radiology, vol. 39, Issue 8, pp. 451-454, Aug. 2004.
Mahnken, A. H., et al., "Measurement of cardiac output from a test-bolus injection in multislice computed tomography," European Radiology, vol. 13, Issue 11, pp. 2498-2504, Nov. 2003.
Mark V/Mark V Plus Injector Operation Manual KMP 805P Rev. B. MEDRAD, Inc, 1990.
McClellan, J.H., "Parametric Signal Modeling," Chapter 1 in Advanced Topics in Signal Processing, Pentice-Hall, Englewood Cliffs, NJ, 1988.
MCT and MCT Plus Injection Systems Operation Manual KMP 810P, MEDRAD, Inc. 1991.
Neatpisarnvanit, C. and Boston, J.R., "Estimation of plasma insulin from plasma glucose", IEEE Transactions on Biomedical Engineering, vol. 49, Issue 11, pp. 1253-1259, 2002.
Bae, K.T., et al., "Peak contrast enhancement in CT and MR angiography: when does it occur and why? Pharmacokinetic study in a porcine model," Radiology, vol. 227, pp. 809-816, Jun. 2003.
Bae, K.T., et al., "Uniform vascular contrast enhancement and reduced contrast medium volume achieved by using exponentially decelerated contrast material injection method," Radiology, vol. 231, Issue 3, pp. 732-736, 2004.
Baker, A.B., and Sanders, J.E., "Fluid Mechanics Analysis of a Spring-Loaded Jet Injector," IEEE Transactions on Biomedical Engineering, vol. 46, No. 2, Feb. 1999.
Becker, C.R., et al., "Optimal contrast application for cardiac 4-detector-row computed tomography," Investigative Radiology, vol. 38, Issue 11, pp. 690-694, Nov. 2003.
Cademartiri, F. and Luccichenti, G., et al. "Sixteen-row multislice computed tomography: basic concepts, protocols, and enhanced clinical applications," Seminars in Ultrasound, CT and MRI, vol. 25, Issue 1, pp. 2-16, 2004.
Cademartiri, F., et al., "Intravenous contrasts material administration at 16-detector row helical CT coronary angiography: test bolus versus bolus-tracking technique," Radiology, vol. 233, Issue 3, pp. 817-823, Dec. 2004.
Coleman and Branch, "Optimization Toolbox for Use with MATLAB, User's Guide," T. Mathworks, Editor 2007.
Dardik, H. et al., "Remote Hydraulic Syringe Actuator," Arch. Surg., vol. 115, Issue 1, Jan. 1980.

(56) References Cited

OTHER PUBLICATIONS

Dawson, P. and M. Blomley, "The value of mathematical modelling in understanding contrast enhancement in CT with particular reference to the detection of hypovascular liver metastases," European Journal of Radiology, vol. 41, Issue 3, pp. 222-236, Mar. 2002.
European Search Report mailed Feb. 21, 2012 in European Patent Application No. 11001045.1.
European Search Report mailed Jan. 30, 2003 in European Patent Application No. 02020247.9.
European Search Report mailed Jun. 17, 1996 in European Patent Application No. 95202547.6.
Final Office Action mailed Jun. 17, 2013, in U.S. Appl. No. 12/519,213, John F. Kalafut et al., filed Jun. 15, 2009.
Final Office Action mailed Jun. 19, 2013, in U.S. Appl. No. 13/186,983, John F. Kalafut et al., filed Jul. 20, 2011.
Final Office Action mailed Mar. 5, 2013, in U.S. Appl. No. 12/519,213, John F. Kalafut et al., filed Jun. 15, 2009.
Final Office Action mailed Oct. 1, 2009, in U.S. Appl. No. 11/691,823, John F. Kalafut et al., filed Mar. 27, 2007.
Final Office Action mailed Oct. 2, 2012, in U.S. Appl. No. 12/519,040, John F. Kalafut, filed Jun. 12, 2009.
Fisher, M.E. and Teo, K.L., "Optimal insulin infusion resulting from a mathematical model of blood glucose dynamics", IEEE Transactions on Biomedical Engineering, vol. 36, Issue 4, pp. 479-486, 1989.
Fleischmann, D. and Hittmair, K., "Mathematical analysis of arterial enhancement and optimization of bolus geometry for CT angiography using the discrete Fourier transform," Journal of Computer Assisted Tomography, vol. 23, Issue 3, pp. 474-484, May/Jun. 1999.
Fleischmann, D., "Contrast Medium Injection Technique," In: U. Joseph Schoepf: "Multidetector-Row CT of the Thorax," pp. 47-59, Jan. 22, 2004.
Fleischmann, D., "Present and Future Trends in Multiple Detector-Row CT Applications; CT Angiography", European Radiology, vol. 12, Issue 2, Supplement 2, Jul. 2002, pp. s11-s15.
Gardiner, G. A., et al., "Selective Coronary Angiography Using a Power Injector," AJR Am J Roentgenol., vol. 146, Issue 4, pp. 831-833, Apr. 1986.
"Disposable Low-Cost Catheter Tip Sensor Measures Blood Pressure during Surgery," Sensor, Jul. 1989.
"Infus O.R. Multi-Drug Syringe Pump with Smart Labels", Bard MedSystems Division Inc., pp. 2693-2696, 2005.
"The Solution for Your IV Formulas," Valley Lab. Inc., E-39-15, 3399, 3400, 2646.
Awai, K., et al., "Aortic and hepatic enhancement and tumor-to-liver contrast: analysis of the effect of different concentrations of contrast material at multi-detector row helical CT.," Radiology, vol. 224, Issue 3, pp. 757-763, 2002.
Awai, K., et al., "Effect of contrast material injection duration and rate on aortic peak time and peak enhancement at dynamic CT involving injection protocol with dose tailored to patient weight," Radiology, vol. 230, Issue 1, pp. 142-150, 2004.
Bae, K.T., et al., "Multiphasic Injection Method for Uniform Prolonged Vascular Enhancement at CT Angiography: Pharmacokinetic Analysis and Experimental Porcine Method," Radiology, vol. 216, pp. 872-880, 2000.
Office Action mailed Jan. 3, 2014 in U.S. Appl. No. 11/691,823.
Search Report and Supplementary European Search Report for EP05849688 dated Mar. 21, 2014.
Blomley, M.J.K. and Dawson, P., "Bolus Dynamics: Theoretical and Experimental Aspects," The Brit. J. of Radiology, 70, pp. 351-359, 1997.
Flegal, K.M., et al., "Prevalence and trends in obesity among US adults," JAMA, 2002, vol. 288, Issue 14, pp. 1-4, 1999-2000.
Gramovish V.V., et al Quantitative estimation of myocardial perfusion in patients with chronic ischaemic heart disease using magnetic resonance imaging, Cardiology, 2004, p. 4-12, No. 89.
Angelini, P., "Use of mechanical injectors during percutaneous transluminal coronary angioplasty (PTCA)," Catheterization and Cardiovascular Diagnosis, vol. 16, Issue 3, pp. 193-194, Mar. 1989.
Awai, K., et al., "Aortic and hepatic enhancement and tumor-to-liver contrast: analysis of the effect of different concentrations of contrast material at multi-detector row helical CT.," Radiology, vol. 224, Issue 3, pp. 757-63, 2002.
Awai, K., et al., "Effect of contrast material injection duration and rate on aortic peak time and peak enhancement at dynamic CT involving injection protocol with dose tailored to patient weight," Radiology, vol. 230, Issue 1, pp. 142-50, 2004.
Bae, K.T., et al., "Multiphasic Injection Method for Uniform Prolonged Vascular Enhancement at CT Angiography: Pharmacokinetic Analysis and Experimental Porcine Method," Radiology, vol. 230, Issue 1, pp. 142-50.

\* cited by examiner

Contrast Osmolality vs Concentration - nonionics

CIN Advanced Setup

Contrast Reduction Rule Setup

*eGFR estimation algorithm one of: [Cockcroft-Gault,MDRD, none]

*Contrast Dose Clamping:
- By eGFR
  * if eGFR < (one of) [ 70 60 50 40 ] ml/min
    reduce contrast volume by:
      [5 10 20 30] %
  OR
    reduce Iodine Dose by:
      [5 10 20 30]%

- By sCr
  *if sCr > (one of) [ 1.5 1.6 1.7 2.0 ] mg/dL
    reduce contrast volume by:
      [5 10 20 30] %
  OR
    reduce Iodine Dose by:
      [5 10 20 30]%

BUN:
  *If BUN:sCr > (one of) [ 10:1 15:1 20:1 ]
    reduce contrast volume by:
      [5 10 20 30] %
  OR
    reduce Iodine Dose by:
      [5 10 20 30]%

Additional or alternative rules .....

Fig. 8B

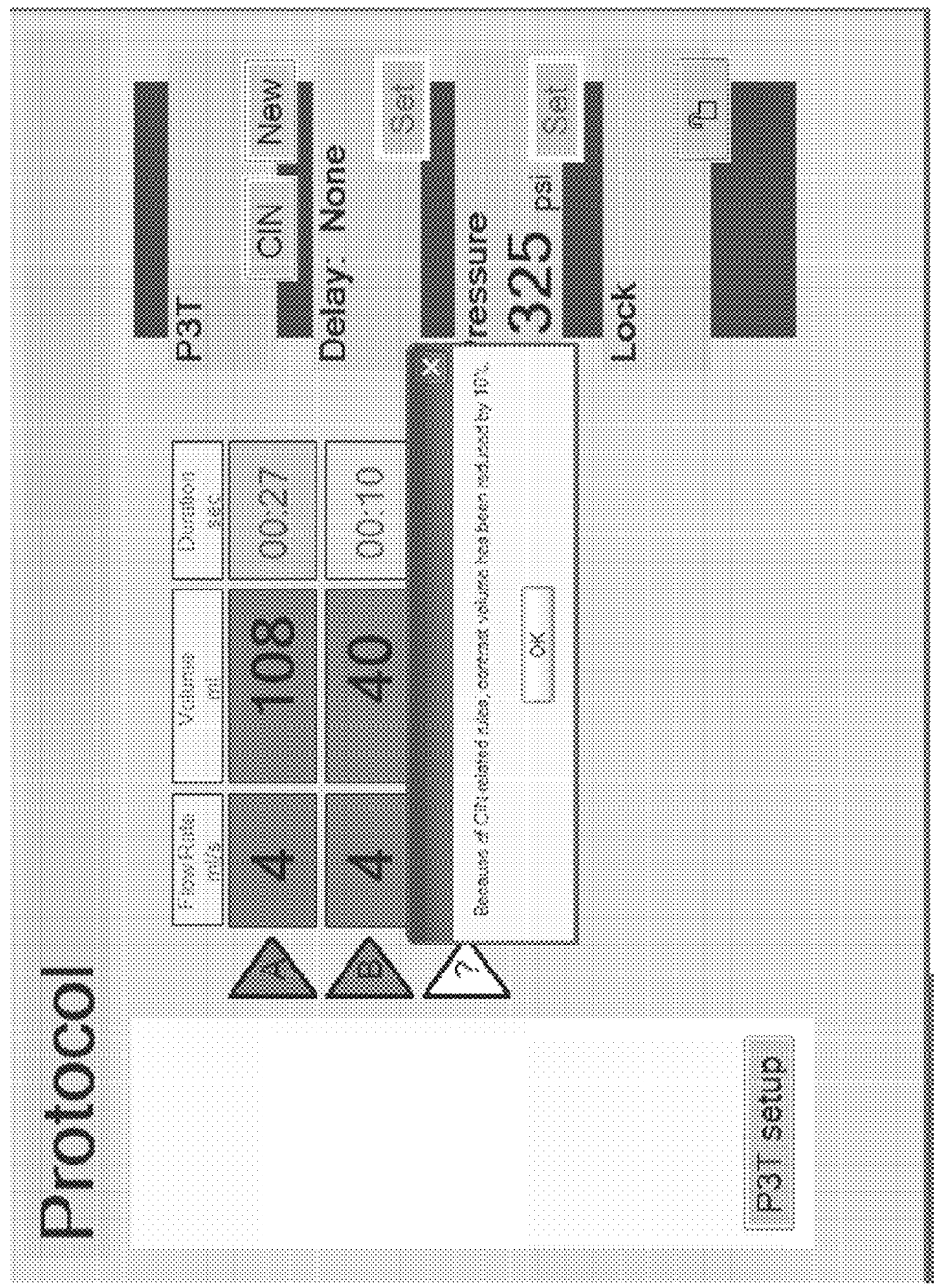

MITIGATION OF CONTRAST-INDUCED NEPHROPATHY

CROSS-REFERENCE TO RELATED APPLICATION

The present application claims the benefit of U.S. Provisional Application Ser. No. 61/110,640 filed on Nov. 3, 2008, the contents of which are incorporated herein by reference in their entirety.

BACKGROUND OF THE INVENTION

The following information is provided to assist the reader to understand the invention disclosed below and the environment in which it will typically be used. The terms used herein are not intended to be limited to any particular narrow interpretation unless clearly stated otherwise in this document. References set forth herein may facilitate understanding of the present invention or the background of the present invention. The disclosures of all references cited herein are incorporated by reference.

Medical imaging procedures often rely on the use of contrast media that is injected into the biological structure to be imaged such that the medical imaging procedure provides more detailed information to a radiologist or other medical personnel responsible for analyzing the medical imagery. Contrast media is often injected into a patient's vasculature prior to the medical imaging procedure and the patient's renal system is thereafter tasked with clearing the contrast media from the patient's bloodstream.

According to conventional radiographic diagnostic imaging techniques such as X-ray procedures, X-rays pass through a target object and expose an underlying photographic film. The developed film then provides an image of the radio-density pattern of the object. Less radio-dense areas produce a greater blackening of the film; more radio-dense, bony tissues produce a lighter image. Effective contrast media for X-ray may be either less radio-dense than body tissues or more radio-dense. The less radio-dense agents include air and other gases; an example of a more radio-dense contrast material is a barium sulfate suspension or iodinated injectable media.

Computed tomography (CT) is superior to conventional radiography in its ability to image, with extremely high resolution, a succession of thin sections of an object at specific points, lines, or planes along the X, Y, or Z axis of the target object. However, because this procedure is also based on the detection of differences in radio-density, requirements for contrast media in CT are essentially identical with those for conventional radiography.

Magnetic resonance imaging (MRI) systems for body imaging operate on a different physical principle. Generally, MRI relies on the atomic properties (nuclear resonance) of protons in tissues when they are scanned with radio frequency radiation. The protons in the tissue, which resonate at slightly different frequencies, produce a signal that a computer uses to tell one tissue from another. MRI provides detailed three-dimensional soft tissue images.

Fluoroscopy imaging systems may provide real-time X-ray images of internal structures based on differences in the radio-density of the imaged object components. As in X-ray procedures, fluoroscopy may be enhanced by the use of more radio-dense contrast media that may be injected into the object being imaged. For instance, in angiography procedures, radio-dense contrast media may be injected into the cardiac vasculature in order to trace the path of blood through the vasculature and determine, for instance, the location of blockages in the cardiac vasculature.

Currently, injection systems used for the dispensing of a contrast media in, for instance, CT, MRI, Ultrasound and/or Angiography/Fluoroscopy medical imaging procedures include interface controls and features limited to the delivery of contrast media within the medical imaging suite. Further, most contrast media is injected into a patient's vasculature for enhancement of imaging procedures and is then physiologically cleared by the renal system through normal nephritic function. During the clearing of contrast media from the patient's body, the serum-borne contrast media places additional burden on renal function until it is cleared. In cases where a patient undergoing a medical imaging procedure using contrast media has a prior history or an unknown pre-existing condition of compromised or impaired renal function, the burden associated with clearing injected contrast media can result in further damage to the kidneys and/or other components of the renal system. Furthermore, in some severe cases, the burden associated with the clearing of iodinated contrast media has destroyed renal function in its totality.

While contrast media used in imaging procedures is generally safe for healthy patients, there are cases of iodinated contrast induced nephropathy resulting from its use in medical imaging patients, as noted above. A representative medical imaging (and optionally treatment) procedure is generally a multistage or step procedure as generally depicted in FIG. 1. In FIG. 1, flowchart 100 illustrates an exemplary imaging procedure from a patient's perspective. In FIG. 1, a first step 110 includes obtaining detailed information concerning the patient such as name, medical history, insurance, next of kin information, etc. This information may be available directly from or confirmed by the patient or from a hospital information system (HIS). The imaging procedure may be conducted as an outpatient procedure or inpatient procedure. The patient is commonly informed about the procedure, discusses any concerns that they might have with the clinical personnel, and signs a consent form. The patient is then dressed appropriately for the procedure and commonly have an intravenous catheter inserted into his/her arm, and possibly is given some medication as preparation.

The patient preparation then continues in an imaging suite at step 120 where the patient is placed on the imaging table, typically given some moderate sedation, and further prepared for the procedure. In a catheterization lab, this step may include generally covering the patient with sterile drapes and preparing a sterile field commonly in the groin area for access to the femoral artery. Blood tests are commonly done to measure clotting time and medication is given to provide for the right level of anticoagulation. The attendant clinical personnel and technicians also prepare various medical devices and systems for use in the procedure, open packages of sterile products and put them onto a sterile table for ready access. Step 120 also includes gaining access to the femoral artery with a sheath, a guidewire, and then a catheter. The guidewire and catheter may be maneuvered some distance before contrast needs to be injected for visualization of their position relative to the patient's vasculature.

When a clinician needs to inject contrast, the contrast imaging phase begins at step 130. Modest "puffs" of contrast are often injected to help the clinician maneuver the catheter into the correct position. Once the catheter is in the correct position, a larger bolus of contrast is typically injected to allow visualization of the vascular tree and identification of any stenosis or other abnormalities of concern. If there is a stenosis or blockage, it can often be treated during the same procedure with angioplasty or insertion of a stent, which involves additional maneuvering of catheters and contrast injections. Once the treatment is competed, no more contrast is injected.

To complete the procedure in the imaging suite at step 140, the catheters are removed from the patient and the wound is closed with stitching of the tissue that had been cut and optionally, the vessel wall. Blood tests may be drawn to ensure that there is sufficient reversal of anticoagulation for the patient to be moved to a recovery area. After being sufficiently stabilized, the patient is wheeled out of the procedure room to the recovery area. The treatment outside the recovery room at step 150 commonly includes observation and monitoring while sedation wears off. Once the patient is coherent enough to understand medical instructions, the patient and any person accompanying the patient are given follow up instructions on wound treatment. The patient then dresses and is prepared for discharge.

The foregoing process can be considered to include three phases: a first or preparation phase 161, a second or injection phase 162, and a third or recovery phase 163. First or preparation phase 161 may be considered to include those steps needed to prepare the patient for a first injection of contrast, including those steps occurring outside and inside of the imaging suite (e.g., steps 110 and 120). Second or injection phase 162 may be considered to encompass the time of first contrast injection to the time of last contrast injection (e.g., step 130). Third or recovery phase 163 may be considered to encompass the time from last injection to a time long enough after the injection phase 162 that it is clear that there are no after effects from contrast injection (including, steps 140 and 150).

Contrast induced nephropathy (CIN) may be defined as a serious degradation of kidney function in patients who have received vascular injections of, for example, iodinated contrast medium. CIN occurs more frequently in patients with known risk factors such as previous administration of contrast, diabetes mellitus, congestive heart failure, obesity, and age-related factors. The condition is relatively rare (less than 5% of the total population receiving contrast), but it occurs with higher frequency (11-50%) and severity in patients whose renal function is already impaired. In more severe cases, CIN can result in the need for dialysis, and it can sometimes result in death. Often, CIN will not become apparent until at least 24-48 hours after contrast administration. This delay in manifestation complicates real-time assessment of kidney function at the time of contrast administration.

The standard of medical care to prevent as well as to treat CIN is "hydration therapy", which includes the intravenous infusion of normal saline at a rate of at least 100 ml/hour for 4 to 6 hours before a contrast-enhanced procedure, followed by several additional hours of intravenous saline. Oral hydration is also recommended for patients at risk of CIN, as an adjunct to intravenous therapy. Fluid volumes between 1-2 liters are believed to stimulate renal excretion of contrast media along with all the additional water.

Although hydration therapy is the standard of medical care to prevent or to treat CIN, slow hydration therapy via intravenous infusion can sometimes result in an overage of fluid in the body, progressing to edema, pulmonary effusion, congestive heart failure, and a worsening of cardio-renal function. It is expected that balancing the urinary output with intravenously infused fluid can reduce the side effects of hydration therapy. A commercial device, RENALGUARD™ (available from PLC Medical Systems, Inc. of Franklin, Mass.) attempts to perform this balancing function over a period of time shorter than the 12-24 hours required by conventional hydration therapy. A drawback of the RENALGUARD™ device is the need to introduce a drainage catheter into the urinary bladder, resulting in patient discomfort and inconvenience for the operator.

Based on the results of clinical trials, CIN can be significantly reduced by intravenous infusion of sufficient fluid volume to promote a glomerular filtration rate (GFR) in excess of 150 ml/hr. (See, for example, Stevens, et al. "A Prospective Randomized Trial of Prevention Measures in Patients at High Risk for Contrast Nephropathy," J of the ACC, Vol. 33. No. 2, 1999, pp. 403-411.) It is currently difficult to measure GFR because of the costs associated with extracting and analyzing blood samples with laboratory equipment (for example, using the RENALYZER™ analyzer available from Provalid AB Corporation of Aldernansgatan, Sweden). A somewhat more practical way to assess kidney function is to measure urine output over time. However, measurement of urine output also requires the use of a urinary catheter to collect kidney output.

In a post hoc analysis, Buckley, et al. showed that imaging of the kidney blood flow by means of dynamic contrast enhanced MRI (DCE-MRI) provided data that correlated well with reference measures of GFR. (Buckley, et al. "Measurement of single kidney function using dynamic contrast-enhanced MRI: comparison of two models in human subjects", J Magi Reson Imaging, 2006 November; 24(5): 1117-23.) Further, Hackstein, et al. showed that total GFR can be measured with CT images of the abdominal aorta with minimally extended triphasic CT in patients without acute renal disorder by using a two-point Patlak plot technique. (Hackstein, et al., "Glomerular filtration rate measured by using triphasic helical CT with a two-point Patlak plot technique", Radiology, 2004 January; 230(1):221-6.)

Given the significant health related problems which may result with contrast induced nephropathy, it is desirable to develop and implement devices, systems, and methods for predicting, preventing and/or mitigating the effects of contrast induced nephropathy. Accordingly, this disclosure is directed to devices, systems, and methods for mitigation of contrast induced nephropathy which may result from the administration of contrast media during medical diagnostic and/or therapeutic procedures such as those described hereinabove.

SUMMARY OF THE INVENTION

The devices, systems, and methods described in detail herein are directed to mitigation of contrast induced nephropathy resulting from injection of iodinated contrast during medical imaging, generally considered to be a diagnostic procedure, and/or during a treatment or therapeutic procedure. The disclosed devices, systems, and methods include patient risk assessment, risk reduction, and treatment of contrast induced physiological reactions during a medical procedure. The principles of the invention described herein are applicable to all medical procedures using any type of contrast media, for example, iodinated contrast in a cardiac catheterization laboratory procedure or a computed tomography (CT) or gadolinium based contrast in magnetic resonance imaging (MRI), as examples.

In one aspect, the present invention provides a system, including a pressurizing mechanism to pressurize a fluid including a contrast enhancement agent for delivery to a patient and a control system in operative connection with the pressurizing mechanism. The control system includes a system to adjust control of fluid injection based upon a measurement of renal function of the patient.

The control system can, for example, be operative to constrain fluid injection to reduce a likelihood of contrast induced nephropathy.

In several embodiments, the system includes an analyzing system to analyze a time enhancement curve resulting from injection of the fluid including contrasting agent to provide a measurement of renal function. The analyzing system can be in operative connection with the control system such that injection of the fluid into the patient can be controlled to reduce the likelihood of nephropathy based, at least in part, on the analysis of the time enhancement curve.

In several embodiments, the control system is operative to control injection of the fluid into the patient to reduce the likelihood of nephropathy based, at least in part, on input of patient specific parameters.

The system can further include an input system for input of patient parameters associated with renal function, the input system being in operative connection with the control system. Such patient parameters can, for example, include at least one of age, body mass index, sex, serum creatinine level in the blood plasma, blood urea nitrogen.

In a number of embodiments, the system includes a system to determine a therapy for the patient after delivery of the fluid to the patient if the patient is determined to be at risk of nephropathy. The determination of a therapy can be based, at least in part, on analysis of a time enhancement curve resulting from injection of the fluid including contrasting agent to provide a measurement of renal function. The therapy can, for example, include a hydration therapy.

In several embodiments, the control system of the present invention is distributed. The control system can also be hierarchical.

The control system can be in communicative connection with an information system (for example, including a hospital information system and/or a picture archive and communication system).

In several embodiments, the control system is in communicative connection with a contrast induce nephropathy therapy system. The therapy system can, for example, include a pump for introducing therapeutic fluids.

In a number of embodiments, the system of the present invention further includes an imaging system, which can be in operative connection with the control system.

In another aspect, the present invention provides an injector system for delivery of a fluid including a contrast enhancement agent to a patient, including: a pressurizing mechanism to pressurize the fluid; and a control system in operative connection with the pressurizing mechanism. The control system is adapted to control of fluid injection based, at least in part, upon a measurement renal function of the patient.

The control system can, for example, be operative to constrain fluid injection to reduce a likelihood of nephropathy.

The injector system can further include an input system for input of data associated with renal function. The data associated with patient renal function can, for example, include at least one of age, body mass index, sex, creatinine level, blood urea nitrogen.

The control system can, for example, be adapted to receive data of a time enhancement curve resulting from injection of the fluid including contrasting agent from the input system to determine an aspect of renal function of the patient.

In several embodiments, the control system is adapted to determine a therapy for the patient after delivery of the fluid to the patient if the patient is determined to be at risk of nephropathy. The determination of a therapy can, for example, be based, at least in part, on analysis of a time enhancement curve resulting from injection of the fluid including contrasting agent to provide a measurement of renal function. The therapy can, for example, include a hydration therapy.

In another aspect, the present invention provides a method of performing an imaging procedure, including: controlling injection of a fluid including a contrast enhancement agent based at least in part upon a determination of renal function of the patient and imaging at least a portion of the patent.

The method can include constraining fluid injection to reduce the likelihood of nephropathy.

The renal function of the patient can, for example, be determined, at least in part, based upon at least one patient parameter. The patient parameter can, for example, include at least one of age, body mass index, sex, creatinine level, and blood urea nitrogen.

The renal function of the patient can also or alternatively be determined, at least in part, based upon analysis of a time enhancement curve of the contrast enhancement agent in at least one region of interest of the patient.

The method can further include determining a therapy for the patient after delivery of the fluid to the patient if the patient is determined to be at risk of nephropathy.

In several embodiments, the determination of the therapy is based, at least in part, on analysis of a time enhancement curve resulting from injection of the fluid including contrasting agent to determine a measurement of renal function.

The therapy can, for example, include at least one of hydration therapy and introduction of at least one nephroprotective agent.

The method can further include determining a therapy for the patient before delivery of the fluid to the patient if the patient is determined to be at risk of nephropathy.

In still a further embodiment, the present invention provides a system for use in an imaging procedure, including: an injector system including a pressurizing mechanism to pressurize a fluid including a contrast enhancement agent for delivery to a patient, an imaging system, and at least one system to adjust at least one parameter of the imaging procedure based upon a measurement of renal function of the patient. The parameter can, for example, be a parameter of the injector system. The parameter can also or alternatively be a parameter of the imaging system.

Further details and advantages will become clear upon reading the following detailed description in conjunction with the accompanying drawing figures.

BRIEF DESCRIPTION OF THE DRAWINGS

FIG. 8B illustrates a continuation of the flow chart of FIG. 8A.

FIG. 9G illustrates an embodiment of a display screen alerting the user to an iodine reduction action taken because the entered renal function parameter (in this example, sCR) exceeded a configured threshold.

DESCRIPTION OF THE PREFERRED EMBODIMENTS

For purposes of the description hereinafter, spatial orientation terms, if used, shall relate to the referenced embodiment as it is oriented in the accompanying drawing figures or otherwise described in the following detailed description. However, it is to be understood that the embodiments described hereinafter may assume many alternative variations and configurations. It is also to be understood that the specific devices, features, and components illustrated in the accompanying drawing figures and described herein are simply exemplary and should not be considered as limiting.

As used herein and in the appended claims, the singular forms "a," "an", and "the" include plural references unless the content clearly dictates otherwise. Thus, for example, reference to "a display" includes a plurality of such displays and equivalents thereof known to those skilled in the art, and so forth, and reference to "the display" is a reference to one or more such displays and equivalents thereof known to those skilled in the art, and so forth.

Figure 1:
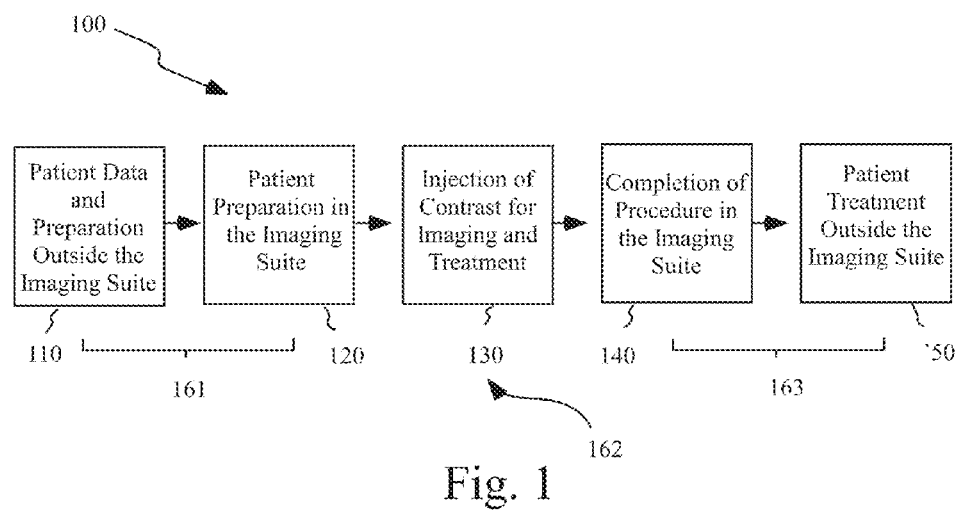
FIG. 1 is a flowchart illustrating the steps of an exemplary imaging procedure from a patient's perspective.

As noted previously, FIG. 1 is a flowchart illustrating the various steps, stages, or phases of an exemplary imaging procedure and is provided to facilitate understanding of the various embodiments of the invention that will now be disclosed. It should be recognized that patients can have multiple medical procedures within a given timeframe and contrast from earlier medical procedures may have a cumulative and contributory detrimental effect when contrast is delivered in subsequent medical procedures. The various apparatus and methods described hereinafter relating to the mitigation of contrast-induced nephropathy in patients in generally applicable to the generic imaging procedure outlined in FIG. 1.

Figure 2:
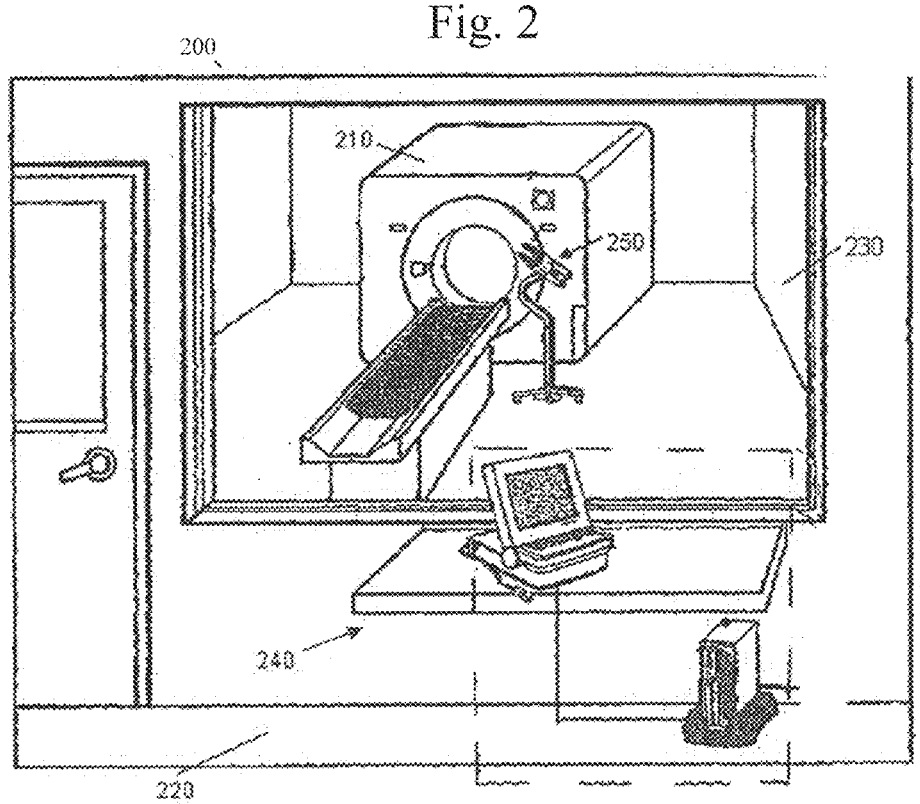
FIG. 2 is a schematic view of a medical imaging system according to one embodiment and provided in an imaging suite in a medical facility.

FIG. 2 shows a medical imaging system 200 according to one embodiment wherein a medical imaging device 210 is located within a medical imaging suite of a hospital, health care facility, and/or research facility. The medical imaging device 210 may comprise, for instance, a computed tomography (CT) scanner, a fluoroscope, a positron emission tomography (PET) scanner, a magnetic resonance (MR) scanner, an ultrasound device and/or other imaging device that may require the dispensing of a contrast media to a patient prior to performing the medical imaging procedure so as to enhance the quality of an image produced by the imaging device 210. As used herein, the term "medical imaging suite" refers generally to a room or collection of rooms within, for instance, a hospital or other health care facility, wherein various devices components of medical imaging system 200 may be located or distributed. The medical imaging suite may further comprise, for instance, a control room 220 where an operator of the medical imaging system 200 may be stationed, as well as an imaging room 230 wherein the medical imaging device 210 and other equipment related to a medical imaging procedure may be located. As shown in FIG. 2, a computer device 240 is located in control room 220 and is desirably operably connected with medical imaging device 210 so as to control the operation of the medical imaging device 210. Accordingly, medical imaging device 210 may be controlled remotely by an operator of the medical imaging system 200 and the medical imaging device 210 may be further in communication with a computer network via wire connection and/or wireless methods such that images provided by the medical imaging device 210 may be sent to the controller computer device 240 and such that the images may be adapted to be viewed by an operator of the medical imaging system 200 and/or stored in a memory device operably connected with the controller computer device 240 in the control room 220. As described herein, medical imaging device 210 may further be configured to be in communication with other components of medical imaging system 200 via, for instance, a computer network, such that data related to a given patient and/or medical imaging procedure may be transferred between the components of the medical imaging system 200 and/or to other electronic devices connected to or otherwise in communication with the computer network.

FIG. 2 also shows a dispensing device 250 located within imaging room 230 for administering contrast media to a patient prior to being subjected to a medical imaging procedure. Dispensing device 250 is advantageously an injection device, such as a power injector, configured to inject contrast media directly into the vasculature of a patient prior to the inception of the medical imaging procedure. In some embodiments, dispensing device 250 may comprise a computer device operably connected therewith, wherein the computer device may be configured to be connected via wire connection or wireless methods to a computer network, such as the computer network associated with medical imaging device 210. Thus, dispensing device 250 may be controlled remotely by an operator of the medical imaging system 200 by, for instance, controller computer device 240 located within control room 220. Accordingly, dispensing device 250 may be located in the imaging room 230 while the operator of the medical imaging system 200 may control the dispensing device 250 from, for example, control room 220 adjacent to the imaging room 230 or located elsewhere within the medical imaging suite. Dispensing device 250 may also be configured to dispense contrast media that is adapted to be ingested orally by the patient being subjected to the medical imaging procedure, such as, for example, liquid iodine.

It may be desirable to co-locate a fluid analyzing device (not shown) within or near the medical imaging suite to receive and analyze a biological fluid sample from the patient so as to determine a level of at least one substance in the biological fluid sample prior to, during and/or after the dispensing of contrast media by, for example, dispensing device 250. Such a biological fluid sample may comprise, for example, a blood sample, urine sample, saliva sample, and/or other biological fluid samples suitable for analysis in the analyzing device. Several suitable embodiments of an analyzing device for this purpose are disclosed in United States Patent Application Publication No. 2006/0074294 to Williams, J R. et al. which is incorporated herein by reference.

Figure 3:
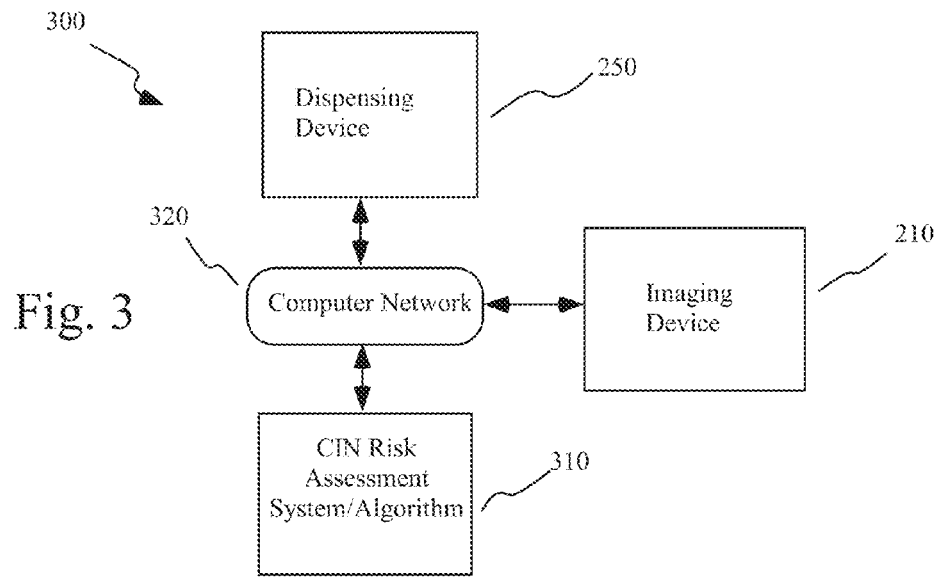
FIG. 3 is a flowchart illustrating a contrast-induced nephropathy risk assessment system according to one embodiment.

Before a contrast-enhanced imaging or therapeutic procedure is performed the risk of CIN is desirably assessed. One source for accessing the risk of CIN is from the medical history and/or the results of lab tests for the patient. This assessment risk information source may, for example, result in limiting the maximum amount of contrast the patient may be given or serve as a guide to recommend an appropriate amount of contrast for the patient. Referring further to FIG. 3, a CIN risk assessment system 300 according to one embodiment is shown. CIN risk assessment system 300 is, for example, a computer-based system that can, for example, estimate the risk of CIN in a patient before a contrast based imaging or therapeutic procedure is performed. In the depicted embodiment of CIN risk assessment system 300, a CIN risk assessment algorithm or program resides, for example, on a computer system 310 that is operably connected to a computer network 320, such as the computer network described previously encompassing or associated with imaging device 210 and dispensing device 250 in FIG. 2. While computer platform 310 may be a separate computer device connected to computer network 320, the CIN risk assessment algorithm or program may also reside on computer device 240 described previously and, thereby, CIN risk assessment capability may be combined with control and operation of imaging device 210 and dispensing device 250 afforded by computer device 240. The CIN risk assessment algorithm or algorithms can alternatively be distributed over two or more computer systems which can, for example, be in communicative connection via computer network 320.

In several embodiments, a CIN risk assessment computer program has information inputs including, but is not limited to: patient past history of contrast usage, if pre-existing renal insufficiency exists, if diabetes exists, age, if the patient is concurrently using nephrotoxic drugs, hydration level, blood pressure, if previous heart failure exists, if contrast allergy exists, if cirrhosis exists, if nephritic syndrome exists, height, weight, body surface area (BSA), creatinine level, body mass index (BMI), blood urea nitrogen (BUN), Kidney Injury Marker 1 & 2, cardiac output, recent urine volume, planned contrast based imaging procedure, and planned contrast type to be used. An information input apparatus can come in many forms such as by keyboard entry, touch screen entry, from computer network 320 which may be, for example, connected to a hospital information system (HIS), electronically stored patient charts, sensors, and local lab test equipment. In several embodiments, computer system 310 may receive real time blood sample, urine sample, saliva sample, and/or other biological fluid sample chemistry feedback to monitor the health of the renal system.

The CIN risk assessment computer program takes the various informational inputs just described and, based on algorithms and/or one or more reference table(s) of past empirical data, provides output, including, for example, an objective CIN risk factor for the patient, a recommended maximum volume of contrast that can be delivered, and/or suggested contrast dilution if any. The algorithms used may include, but are not limited to, the Cockroft-Gault formula, modification of diet in renal disease (MDRD) formula, and the use of past case results. CIN risk assessment system 300 can, for example, output CIN risk assessment information on, for example, a display screen associated with computer device 240. Such CIN risk assessment information may include, as indicated, a recommendation of the maximum amount of contrast to be given to the patient, dilution percentage (if any), as well as an objective indication of the risk of CIN based on the informational inputs. While the display screen may be a computer screen, other display technologies may be employed such as LCD, CRT, and plasma screen displays located, for example, within the control room 220 of medical imaging system 200 shown in FIG. 2. Moreover, CIN risk assessment information can be sent over computer network 320, for example, a local area network (LAN) or a wide area network (WAN), electronically to be added to the patient's medical record or chart and/or be provided as safety inputs to imaging device 210 and dispensing device 250 in medical imaging system 200. Further, CIN risk assessment information may also be output through audio means so that attending medical professionals can get timely CIN risk assessment information and/or warnings in an appropriate manner, such as in the vicinity of the imaging room 230 or control room 220 where contrast is to be administered. A networked CIN risk assessment system 300 allows for easy software updates and for receiving medical history post contrast administration to, for example, refine and improve the CIN risk assessment algorithm. The location of the CIN risk assessment system 300 may have the CIN risk assessment program residing in any suitably connected computer platform including but not limited a hospital server, a patient bedside instrument, and/or within one or the other of the medical imaging device 210 and dispensing device 250 in medical imaging system 200 of FIG. 2. If the CIN risk assessment program is located in computer memory of dispensing device 250 or in communication therewith, CIN risk assessment information can, for example, be used to automatically restrict the use (e.g., volume) of contrast delivered to a patient and thereby provide an important safety check during the imaging procedure. This location for the CIN risk assessment program has an additional benefit in that dilution rates could be programmed into the dispensing device 250. The CIN risk assessment program may also be extended to include patient-specific information on patient disease state, treatment history, physiologic state, contrast dosing history (described further herein) or other patient related parameters or factors that impact the potential risk of CIN or other adverse events. In addition, CIN risk assessment system 300 may be constructed to allow the clinician to choose from a variety of risk models and response behaviors, depending on what the clinician believes is most appropriate for the patient. CIN risk assessment 300 can also provide a suggested risk model based, for example, upon patient data and/or procedure information.

In certain medical procedures (for example, contrast enhanced CT or X-ray procedures), there is often little time to assess patient CIN risk or other reactions to the injected contrast agent. Since the risk of CIN may be related to previous contrast dose or "loading" of the patient or the presence of other drugs in the patient, it is desirable to know the contrast dose history for a particular patient for the clinician to use as a factor when assessing patient CIN risk. The knowledge of past contrast dose exposure (and possibly response thereto)

may be especially useful when a patient must undergo multiple contrast-enhanced procedures within a relatively short time period (for example, one to two weeks) or several procedures within a moderate time period (for example, several procedures per month). For example, if a patient had a contrast enhanced procedure within the last 24 to 48 hours, depending on the patient, the renal system may be at additional risk as a result of long clearance times for some agents and recovery time for the renal system.

Another informational input to the CIN risk assessment algorithm in CIN risk assessment system 300 of FIG. 3 may relate contrast dose history to a given level of risk for a particular patient. In general, risk of CIN increases with contrast dosing history and time of administration relative to the current dose. There are several ways to identify the dosing history of a patient. For example, the patient may be associated with a data carrier device which includes an electronic medical record (EMR) with information about the contrast dose and timing of previous contrast administration. Alternatively, the information regarding the patients contrast dose history may be captured physically on the patient, through marking technology, such as indelible inks, fading inks, removable tags that stick to the skin, or patient wearable labels. Patient contrast dose and timing may also be stored (and accessible) as part of the image data (for example, within a picture archive and communication system or PACS), radiology information system (RIS), hospital information system (HIS), local area network (LAN), wide area network (WAN), or global Internet connected information system, which may contain the patient's electronic medical record. In addition, the contrast dose history and other information may be associated with a unique patient identifier. This unique identifier may then be used to lookup additional information associated with that particular patient.

For example, if contrast dose and history exceeds some set amount, as determined by a clinician or other means such as a standard or guideline, the contrast delivery system (for example, dispensing device 250 in system 200 of FIG. 2) may provide the operator with an alert or automatically adjust the contrast injection parameters such as total contrast dose or dilution to reduce the potential risk of CIN. In addition, CIN risk assessment system 300 of FIG. 3 may be used to track the additional cumulative contrast dose delivered to the patent at the time of imaging and factor in previous contrast dose history information to provide feedback to the clinician or end contrast delivery when a given cumulative dose history limit has been exceeded. Additional information that may be useful includes, but is not limited to, historical and current clearance rates and renal output, if available. In another variation, the operator may also receive a real-time update of cumulative contrast dose history and CIN risk level during the procedure. Also, once the imaging procedure has been completed, the patient's medical record may be automatically updated with the most recent contrast dose and timing information as well as with information on renal function determined in a previous imaging procedure using methods described herein.

Another way to minimize the risk and incidence (CIN) is to monitor the real-time contrast load in the patient, which is the dose of contrast that still remains systemically within a patient's body, before, during, or after contrast agent administration. This real-time contrast load may, for example, be used as a parameter or informational input to the CIN risk assessment system 300 and, more particularly, the algorithm residing in computer system 310 (and/or computer device 240 in system 200 of FIG. 2) to control or modify the imaging procedure or patient treatment or to provide the clinician with information about the patient's status. Contrast load in the patient may be determined in a number of ways, for example, by monitoring or measuring the amount of contrast agent administered to the patient, tracking the time since administration, through measurement and/or monitoring of the contrast clearance rate and through tracking or monitoring of contrast distribution in situ using imaging system 200. In the disclosure of United States Patent Application Publication No. 2006/0074294, for example, a portable chemistry analyzing device is provided for determining the level of level of blood urea nitrogen (BUN), creatinine, or combinations thereof in the biological fluid sample, with this device residing locally in the control room area of an imaging suite. Such a device may be used in CIN risk assessment system 300 for contrast load assessment during an imaging procedure.

Contrast load assessments or measurements may be made before, during, and after an imaging procedure. For example, before the procedure, if the measured contrast load is high, the clinician may be alerted by CIN risk assessment system 300 of increased risk with further administration of contrast agent, or the clinician may receive guidance to use a different concentration or type of contrast agent. Guidance may be in the form of an "expert-system" or software based rules-engine provided as part of the CIN risk assessment program or algorithm that uses information about the patient physiologic characteristics (age, weight, sex, disease state, etc.), contrast load, and other information to provide guidance to the clinician with respect to patient risk, care, and treatment. The guidance may be based on formal rules or heuristics developed around patient treatment relative to contrast load.

During and after the procedure, for example, the clinician may be provided with real-time feedback or a recommended course of treatment or information on recommended medications to be administered to treat the high contrast dose. As another example, medications such as renal vasodilators or fluids for hydration may be automatically administered when the measured contrast load is high, or iodine dialysis equipment may be automatically activated. Nephroprotective agents such as sodium bicarbonate and/or acetylcysteine can be administered (for example, in combination with hydration with sodium chloride solution/saline). As another example, injection or delivery of additional contrast agent dose may be reduced or delayed by some recommended time to reduce risk. After the imaging procedure, the clearance rates of the contrast agent may be monitored to track renal function and provide input to any therapies or changes in patient care as a result of the measurement.

Currently contrast dose or load in the patient may be estimated in several ways. One estimation method forming part of the present invention is to directly measure the concentration, such as through the use of infrared (IR) or X-Ray sensors, chemical sensors, or from the imaging system used, such as an X-Ray or CT scanner. X-Ray contrast agents are iodine-based compounds with specific IR absorption spectra that differ from the spectra of blood or water. A "clip-on" infrared or X-ray based non-invasive sensor may be attached to the subject's finger or earlobe to obtain a local blood concentration measurement for contrast agent by measuring the level of energy absorption through some region of tissue. A suitable sensor for this purpose is disclosed in U.S. Pat. No. 5,840,026 and U.S. Patent Application Publication Nos. 2008-0097197 and 2007-0255135 incorporated herein by reference. Chemical concentration identification through infrared spectroscopy, and other imaging is well known for other applications, such as a capillary blood oximeter (or optical plethysmograph) for oxygen saturation measurements of blood.

In another embodiment, contrast concentration sensing may be performed by optical or electro-chemical sensors attached to a catheter placed within the vascular system. As blood containing the iodine based imaging compound flow over the sensor, the local concentration in the blood may be measured as a way to estimate total dose to the patient. In another embodiment, a measurement of density changes in image opacification using "Hounsfield Units" or some other equivalent image density/intensity measurement with the imaging system within some region of interest, such as in the kidneys, may be used to estimate the amount of contrast agent in the patient. Fluoroscopy or rotational angiography may be used in conjunction with an image processing system to measure these changes. Computer images maps of Hounsfield units may be used to show the excretion of contrast by kidneys and flow through the ureters into the bladder.

In addition to patient contrast load, contrast clearance rate information may also provide information that can be used to reduce the risks associated with CIN. For example, clearance rate information coupled with contrast dose and contrast dose timing information may be used to predict the time needed for sufficient levels of contrast to clear before it is safe to administer more contrast to the patient. Contrast clearance rate calculation may form part of the algorithm associated with the computer system 310 in CIN risk assessment system 300. Also, clearance rate information may be used to monitor renal function after contrast administration in addition to creatinine level measurements as a secondary check. Sudden drops in the rate of iodine or by-product excretion may indicate important changes in renal function. Clearance rates may also be monitored by sensing the level of the concentration iodine or contrast agent by-products in urine. This sensing may occur while in the bladder, or the concentration of by-products may be measured once excreted from the body through a urinary catheter or some other means. As mentioned previously, iodine or by-product concentration in the bladder or urine may be measured by IR optical, chemical, electro-chemical, or other sensing means. Measurements over time may be used to construct clearance rate time-curves that may provide insight into kidney function and provide input regarding the time required until there is sufficient recovery for further contrast enhanced imaging.

It is well-known in the medical field to perform a blood test whereby blood urea nitrogen (BUN) and creatinine levels can be measured as a method for assessing renal function and a patient's ability to safely clear contrast media. However, current medical imaging systems, such as contrast media injection equipment in existing medical imaging suites, do not typically provide for the clinical biological fluid chemistry measurements of BUN and creatinine to pre-screen and/or qualify a patient for contrast media injection. In addition, the measurements of BUN and creatinine levels are not made on a substantially real-time basis in the medical imaging suite as part of a medical imaging procedure. For example, in current inpatient hospital settings, the clinical chemistry laboratory is typically located in a different area of the hospital from the radiology department. As such, either the patient or a biological fluid sample from the patient must be forwarded to the clinical chemistry laboratory for processing. In the case where a biological fluid sample is transferred to the clinical laboratory, additional phlebotomist time and expense is incurred. Thereafter, the results must be reported and either transmitted directly to the radiologist from the lab, or indirectly to the radiologist through the referring physician prescribing the radiographic exam in the first place. Similar obstacles are encountered for patients requiring pre-qualifying biological fluid BUN/creatinine analysis prior to undergoing contrast enhanced radiographic examination in an outpatient radiology practice. In this case, the clinical laboratory and radiology office may be in separate buildings separated by large geographic distances. The foregoing described methods for determining contrast concentration sensing and/or contrast clearance rates may be provided locally in the imaging suite according to the present invention and overcome these physical limitations. Further, measurements can also be made via a point-of-care (POC) system such as the EZ CHEM™ blood analyzer system available from by E-Z-EM, Inc. of Lake Success, N.Y. or the iSTAT® handheld analyzer system (available from Abbott Laboratories of Abbott Park, Ill.).

Another feature now to be described relates to evaluating kidney function and risk of CIN contemporaneously with an imaging procedure via the non-invasive imaging of contrast medium in tissue and/or blood. Application of mathematical modeling techniques to these images and, optionally, other non-imaging information specific to the patient, provides quantitative assessment beyond what is available in current clinical practice.

Figure 4:
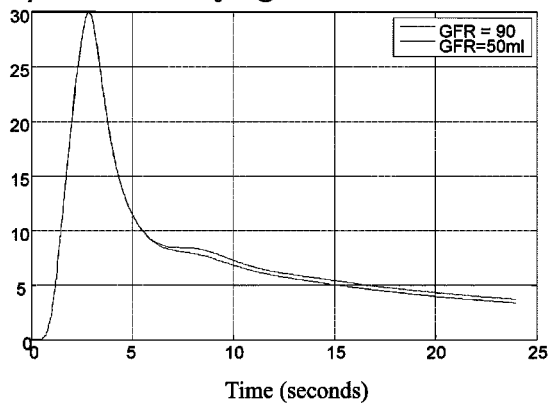
FIG. 4 illustrates typical simulated time-density curves of contrast in the aorta for two different glomerular filtration rates (90 ml/min and 50 ml/min).

In CT imaging, quantitative information about renal blood flow may be obtained from the image intensity (Hounsfield units) measured in a region of contrast enhancement. The typical time-density curve of contrast in the aorta follows the pattern illustrated in FIG. 4. A large peak of contrast density is measured as contrast media makes its way from the venous circulation, through the lungs and heart and into the arterial blood flow. A second peak is seen during the second pass of blood through the circulation. Subsequently, a gradual reduction of contrast is noted as the material is filtered from the blood by the kidneys. One or more characteristics (for example, slope) of this portion of the "washout" curve may be associated with the glomerular filtration rate or GFR achieved by the kidneys. For example, the slope of the curve will be greater in the case that contrast is being removed at the normal rate, and reduced in the case of impaired kidney function. The washout curve may, for example, be observed in a number of regions of interest (ROI's) including, but not limited to, the aorta, in the renal arteries, the ureters, and/or in the urinary bladder.

In several embodiments of the present invention, non-parametric and/or parametric models of renal function are applied in the prediction of CIN and incorporated within systemic approach for management of contrast media delivery. These embodiments of the systems and methods of the present invention can be used in both minimizing the probability of CIN and to provide a personalized treatment and/or a prophylactic paradigm as necessary. For example, this approach may be used to prospectively determine if a patient to undergo radiological examination is at risk of CIN and for the management of that patient. In several embodiments, one or more patient physiological parameters that may provide an indication of whether the patient is "at risk" (or a greater than normal risk) for CIN are first measured. For example, a measurement of the patient's serum creatinine levels and/or the blood urea to nitrogen (BUN) ratio can be made either via standard laboratory assay methods or using a bedside monitoring technology, such as the EZCHEM™ blood analyzer system available from by E-Z-EM, Inc. of Lake Success, N.Y. or the iSTAT® handheld analyzer system (available from Abbott Laboratories of Abbott Park, Ill.) as described above. Current clinical practice suggest that patients with serum creatinine levels>1.3 mg/dL are considered "at risk" of developing CIN. An initial assessment of CIN risk can be made prior to the beginning of an injection/imaging procedure. If the risk is unacceptable, a decision can be made to forego the procedure.

A better prognosticator of CIN risk than serum creatinine level or BUN alone is the glomerular filtration rate. An initial estimate of GFR may, for example, be made by consulting standard look-up tables that treat serum creatinine as an independent parameter along with, for example, BMI, age, and sex. In the methodology depicted schematically in FIG. 5A, an "off line" (or pre-injection procedure) measurement of, for example, serum creatinine (and/or BUN) as discussed previously, can be made, for example, either at the bedside or reported from laboratory tests.

As described previously in connection with FIGS. 2-3, input data can, for example, be entered or populated via a manual input system (including, for example, a keyboard entry, a touch screen, a mouse etc.) or from a network storage device in communicative connection with computer system or systems (for example, computer system 310) on which a CIN risk assessment algorithm or program resides. This algorithm or program can, for example, include an algorithm wherein GFR and/or other indicators as described above are initially used as a basis for identifying risk of CIN in a patient about to undergo contrast injection. As further described previously, the program or algorithm may be located completely or partially on an injector (for example, dispensing device 250), on an imaging device (for example, imaging device 210), or on a scanner console and/or on a separate component (such as computer device 240).

Figure 6:
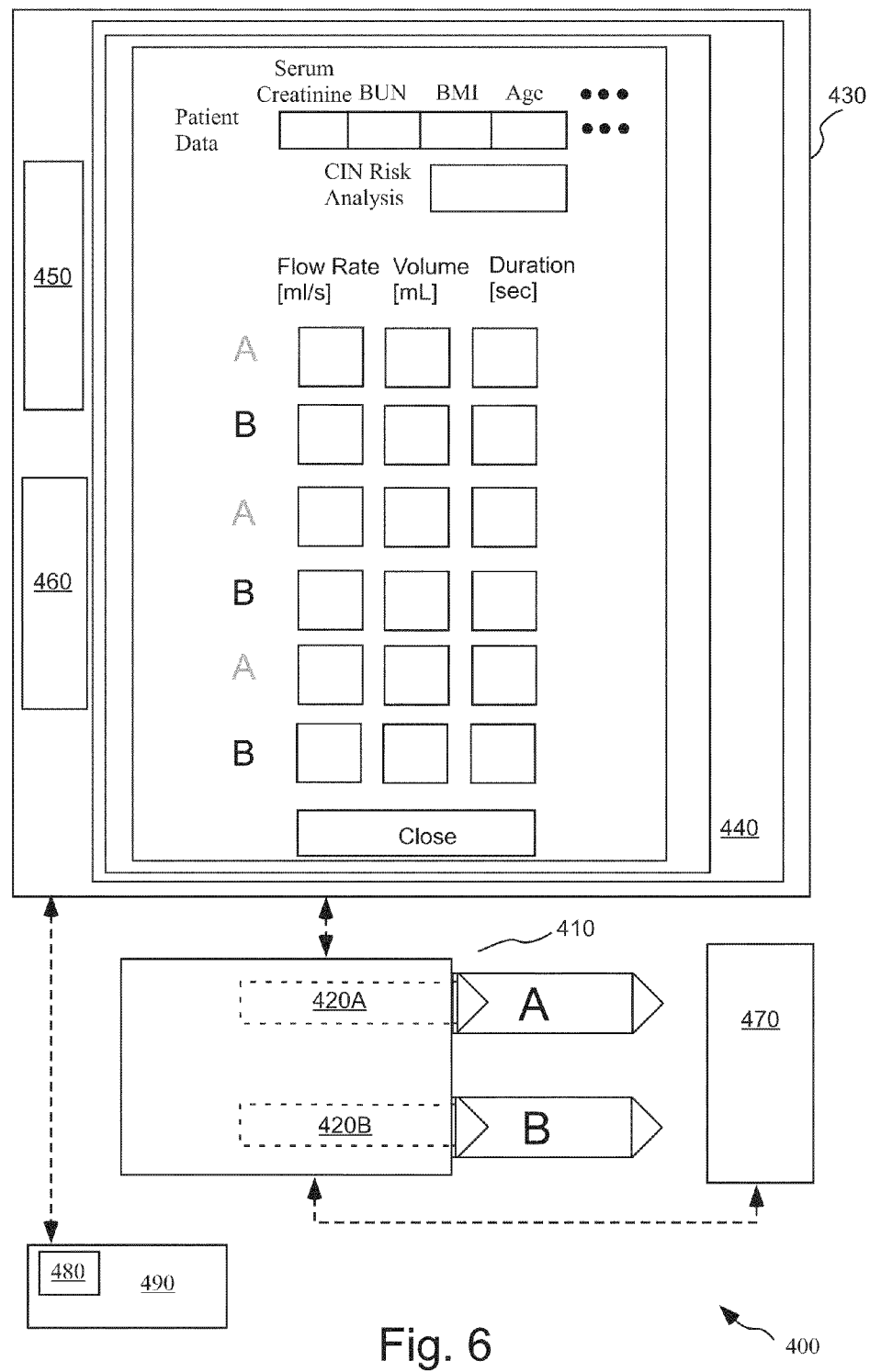
FIG. 6 illustrates one embodiment of a system of the present invention.

Referring to FIG. 6, a system 400 is illustrated including a dual-syringe power injector system 410 is shown as an embodiment of dispensing device 250 described previously in connection with FIG. 2. For example, syringe injector system 410 may be similar to that disclosed in U.S. Pat. No. 6,643,537 and United States Patent Application Publication No. 2004-0064041, the disclosures of which are incorporated herein by reference. FIG. 6 shows two fluid delivery sources, source "A" and source "B", which may be syringes as schematically illustrated. Syringes A and B are operable to introduce a first fluid and/or a second fluid, for example, contrast enhancement fluid, saline etc., into a patient independently, for example, simultaneously in different volumetric flow proportion to each other, or sequentially or subsequent to each other. Injector system 410 comprises a first drive member 420A for pressurizing syringe A and a second drive member 420B for pressurizing syringe B. Injector system 410 includes a control system or controller 430 in operative connection with pressurizing mechanism 420 whereby operation of drive members 422A, 422B may be controlled to control injection of fluid A, for example, contrast medium from syringe A and injection of fluid B, for example, saline from syringe source B. Control system 430 can, for example, include a user interface including a display 440. In the illustrated embodiment, display 440 illustrates representative data entered for CIN risk analysis, such as, serum creatinine, BUN, BMI, age, sex etc., an indication of the result of CIN risk analysis, and areas for display of parameters for injection flow rate, injection volume and injection duration for, for example, three phases of injection or fluid A and/or fluid B. The parameters for one or more such phases can, for example, be entered by an operator and/or populated using the parameter generation systems and methods of the present invention. Various embodiments of parameter generation systems that do not consider CIN risk analysis are, for example, also disclosed in Published PCT Application No. WO/2006/058280, Published PCT Application No. WO/2006/055813, the disclosures of which are incorporated herein by reference. The CIN risk analysis methods and systems of the present invention can, for example, be used in connection with one or more such parameter generation systems. An operator may be provided with the option to adjust and/or override parameters generated automatically by the system. Control system 430 can also include a processor 450 (for example, a digital microprocessor as known in the art) in operative connection with a memory 460. The CIN risk assessment program can, for example, be stored in memory 460 and executed by processor 450 as is well known in the computer field.

System 400 further includes an imaging system 470 which may be associated with pressuring mechanism 470 and may be, for example, a CT system, a Magnetic Resonance Imager (MRI) system, an ultrasound imaging system, or other imaging system as known in the art. Injector system 410 may be in communicative connection with imaging system 470 and one, a plurality, or all of the components of the injector system 410 and imaging system 470 may be integrated or incorporated into another or be separate components that are placed in communicative connection with each other and/or additional system components. One embodiment of distribution of the position of various elements of system 400 is illustrated in FIG. 5B.

GFR estimation equations and/or lookup tables can, for example, be programmed into CIN risk assessment algorithm or program within memory 460 of control system 430 of injector system 400. As represented by stages A and B in FIG. 5A, the injector system 400 can, for example, make an initial CIN risk determination based on a threshold criterion, which can be configurable by the clinician and/or preset, as to whether the patient may be at risk for CIN. Similarly, the serum creatinine level or BUN alone could be used to trigger a warning to the operator. If it is determined that there is an unacceptable risk of CIN, the procedure can be stopped. If there is a risk of CIN, but the risk is acceptable or manageable, the CIN risk assessment algorithm or program can, for example, make suggestions, for example, for constraining the injection protocol to reduce total contrast volume or iodine load to that patient. The CIN risk assessment algorithm or program can also populate the injection protocol with injection parameters for one or more phases of the injection.

As used herein with respect to an injection procedure, the term "protocol" refers generally to a group of parameters for a procedure (for example, an imaging procedure involving the injection of a contrast enhancement fluid or contrast medium) Injection parameter can, for example, include as flow rate, volume injected, injection duration, contrast agent concentration etc. that define, for example, the timing of, amount of, and/or the nature of fluid(s) to be delivered to a patient during an injection procedure. Such parameters can change over the course of the injection procedure. As used herein, the term "phase" refers generally to a group of parameters that define, for example, the timing of, amount of, and/or the nature of fluid(s) to be delivered to a patient during a period of time (or phase duration) that can be less than the total duration of the injection procedure. Thus, the parameters of a phase provide a description of the injection over a time instance corresponding to the time duration of the phase. An injection protocol for a particular injection procedure can, for example, be described as uniphasic (a single phase), biphasic (two phases) or multiphasic (two or more phases, but typically more than two phases). Multiphasic injections also include injections in which the parameters can change continuously over at least a portion of the injection procedure.

Scanner parameters that can be determined include, but are not limited to, the amount of radiation transmitted to the patient, power inputs (for example, voltage or current), timing (for example, scan start time, stop time, delay time and/or duration).

Figure 5A:
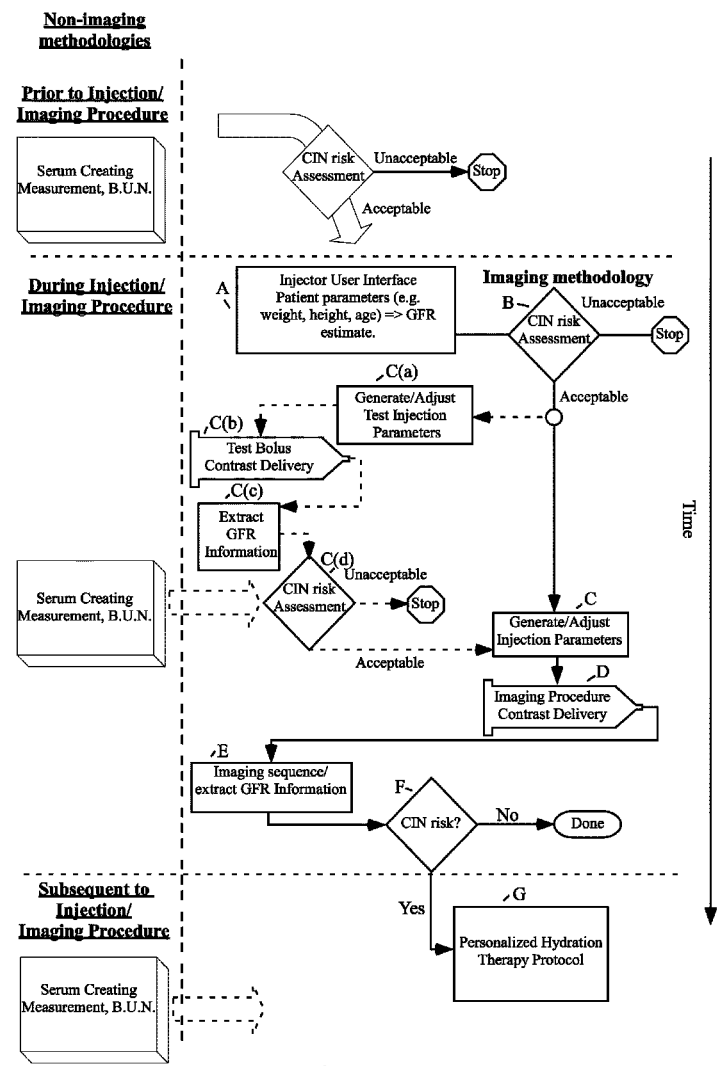
FIG. 5A illustrates a flow chart of an embodiment of a system of the present invention for preventing or reducing the severity of contrast induced nephropathy.
Figure 5B:
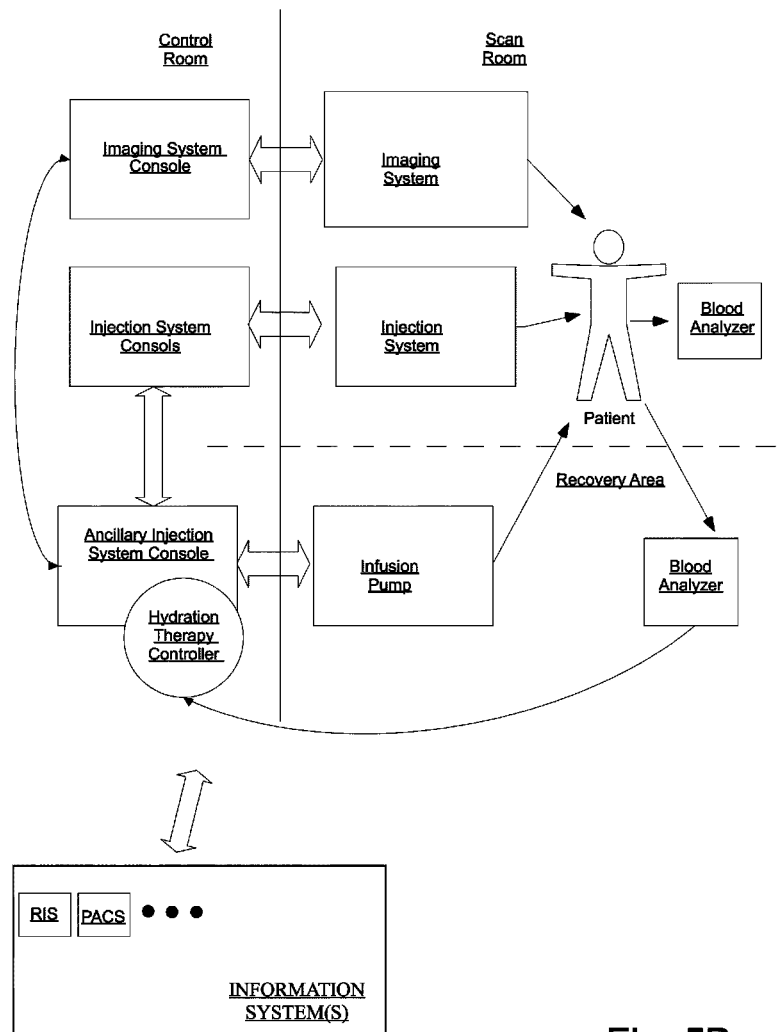
FIG. 5B illustrates one embodiment of the positioning of various elements of a system of the present invention.

As illustrated in FIG. 5A, some injection/imaging procedures can include a test injection or test bolus which can be used to, for example, to determine the injection parameter for a diagnostic/imaging injection as described in Published International Patent Application Nos. WO 2006/055813, WO/2008/085421, WO/2008/082937, WO/2006/058280, PCT International Patent Application No. PCT/US2008/67982 and United States Application Publication Nos. US2008/0097197 and US2007/0255135, the disclosures of which are incorporated herein by reference. As described above, the CIN risk assessment features set forth in this disclosure can, for example, be incorporated within or combined with one or more of the methods and/or systems of such injection parameter generation systems or any portion of such methods and/or systems. Other injection/imaging procedures may include only a diagnostic/imaging injection or bolus. In FIG. 5A, an optional test bolus procedure is illustrated with a dashed line path. In a first stage C(a) of the test bolus procedure parameters, for example, flow rate, volume etc., may be generated/adjusted, considering the results of CIN risk assessment stage B. Alternatively, in procedures with no test injection phase, parameters from one or more phases of a diagnostic injection may be generated or adjusted considering the results of CIN risk assessment stage B at stage C.

After generation of injection parameters in the test injection phase, the injection is performed at stage C(b). GFR information can be extracted from a resultant time enhancement curve as set forth at stage C(c). At this point another CIN risk assessment C(d) can occur at least in part on the basis of GFR information extracted from the enhancement curve. At any point before, during, or after an injection/imaging procedure, non-imaging information regarding CIN risk can be obtained as described previously, for example, by measuring creatinine levels and/or B.U.N. and be input into the system either manually or electronically. In the risk of CIN is deemed to be unacceptable at stage C(d), the procedure can be stopped. If the risk of CIN is acceptable, a diagnostic injection protocol can be generated at stage C, considering the results of CIN risk assessment stage B and stage C(d).

Figure 7:
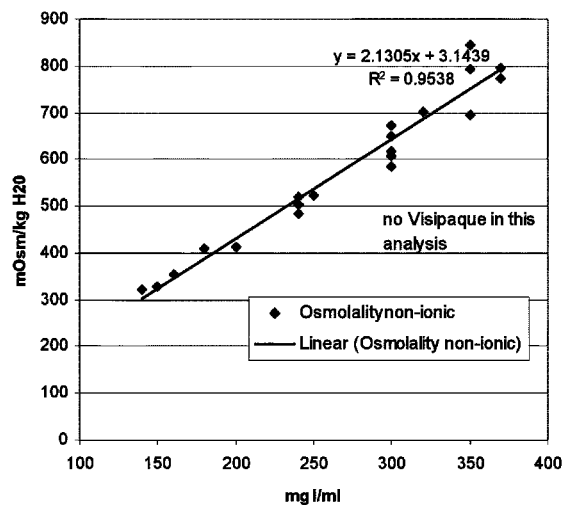
FIG. 7 illustrates the linear relationship between contrast material osmolality and iodine concentration.

In several embodiments of CIN risk assessment programs of the present invention, a "constrained protocol generation engine or system" is used. For example, in one possible implementation of such a constrained protocol generation engine or system, adaptive dilution of the contrast agent may be recommended. It is known that the osmolality of non-ionic X-Ray contrast is linearly related to the iodine concentration of the drug. FIG. 7 is graph which plots the osmolality of commercially available, non-ionic X-Ray contrasts versus their iodine concentration. The osmolality of human blood is typically 290 mOsm/kg H20. Because of the osmotic regulation function of the renal system, it has been suggested that the hyperosmolality of X-Ray contrast media is a causal factor in the etiology of CIN. By diluting the contrast agent to the point that it is, for example, iso-osmolar or nearly iso-osmolar to blood prior to injection, the assertion is that CIN frequency and severity will be reduced. The dilution of the contrast media, however, reduces the concentration of the contrast medium. A reduction in contrast media results in a reduction of peak contrast enhancement if the diluted species is injected at the same volumetric flow rate as the non-dilute species. Contrast dilution to achieve iso-osmolarity is, for example, discussed in PCT International Patent Application No. PCT/US07/70497, filed Jun. 6, 2007, the disclosure of which is incorporated herein by reference.

In several embodiments, an adaptation to the injection protocol's administration flow rate is determined by control system 430 of the injector system 400 to generate equivalent peak enhancement. The clinician can be alerted to the fact that a reduction in contrast enhancement may result by, for example, either clamping the injection volume or contrast concentration. The use of optimized contrast delivery systems is disclosed, for example, in Published International Patent Application Nos. WO 2006/055813, WO/2008/085421, WO/2008/082937, WO/2006/058280, PCT International Patent Application No. PCT/US2008/67982 and United States Application Publication Nos. US2008/0097197 and US2007/0255135, and can mitigate the image contrast enhancement reduction.

Once the contrast injection (stage D) is completed, a measurement of serum creatinine, GFR, B.U.N., or other functional assessment of renal capacity can, for example, be made to help in determining if the patient is likely to experience CIN complications. One parameter to assist the decision process is the analysis of time enhancement data generated via, for example, X-Ray, MR, or nuclear scanning (stage E in FIG. 6) of, for example, the patient's abdominal aorta after the contrast medium has circulated throughout the body several times. An estimate of GFR may be made from identification techniques applied to the imaging data. A parametric estimation fit to a pre-existing model structure may, for example, be applied (assuming the model is a priori identifiable) and/or a non-parametric model fit can be applied to the data. In either case, the extracted GFR information may be used to validate the upfront estimation of GFR. Analysis of the imaging data may also be used to make a determination between a "normal" patient and one in which CIN is suspected. For example, one or more features of the enhancement curve during the extinction phase may differentiate a patient at increased CIN risk from a "normal" patient. As described previously, one such feature is the down slope of the extinction curve parameterized by $\alpha$ in $e^{-\alpha t}$. FIG. 7, for example, displays the result of numerical simulation of the Bae full body PBPK model in which the GFR was changed from 90 ml/min to 50 ml/mm, holding all other parameters constant. (See Bae, K. T., J. P. Heiken, and L A. Brink, "Aortic and hepatic contrast medium enhancement at CT. Part I. Prediction with a computer model," Radiology, 1998, 207(3): p. 647-55.) A small but measurable difference in the enhancement curve morphologies are illustrated in FIG. 7.

Assuming the patient is at risk of developing CIN (determined at stage F of FIG. 5A), a further stage G can, for example, include generation of a per-patient hydration/intervention and/or other therapeutic protocol. The information of GFR estimated by any means described previously may, for example, be used in determining the proper volume of fluid to administer to the patient after the contrast enhanced radiological procedure. The GFR estimates, etc, may, for example, be electronically transmitted to one or more control devices 480 associated with one or more infusion pumps 490 which are depicted in FIG. 6. Such infusion pumps 490 may be controlled by control system 430 of injector system 400. Infusion can, for example, start in the imaging room (such as the imaging room shown in FIG. 2) or in a location separate from the scanner.

Figure 8A:
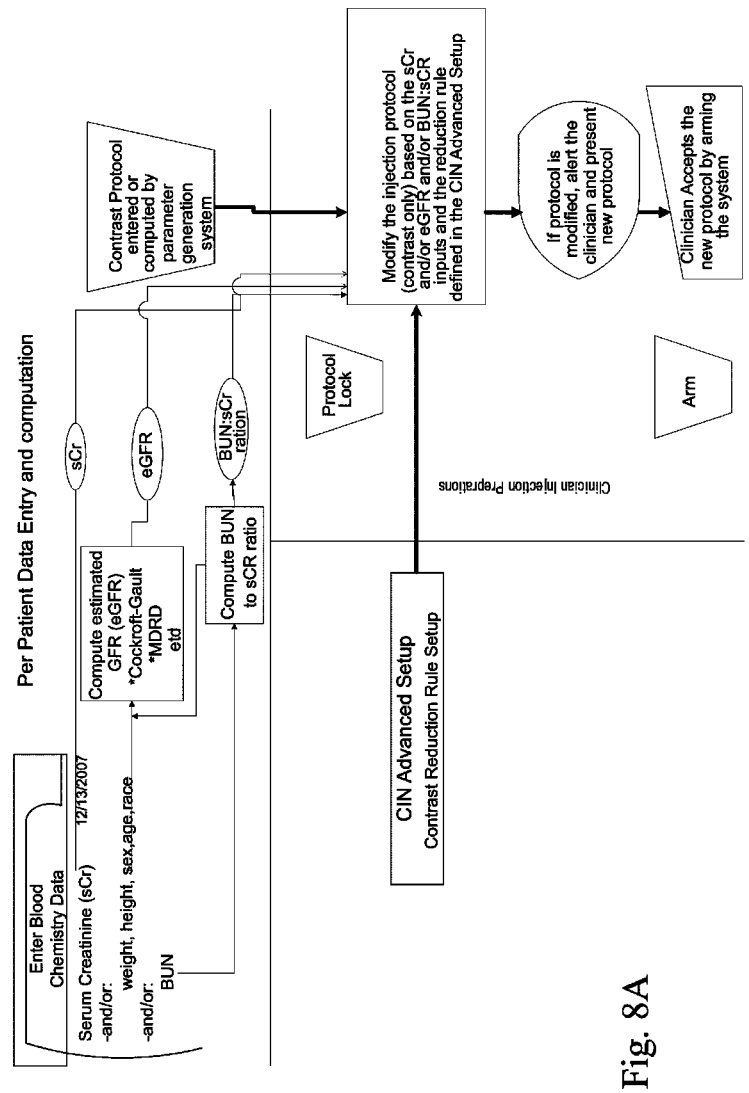
FIG. 8A illustrates a flow chart of another embodiment of a system of the present invention.
Figure 9A:
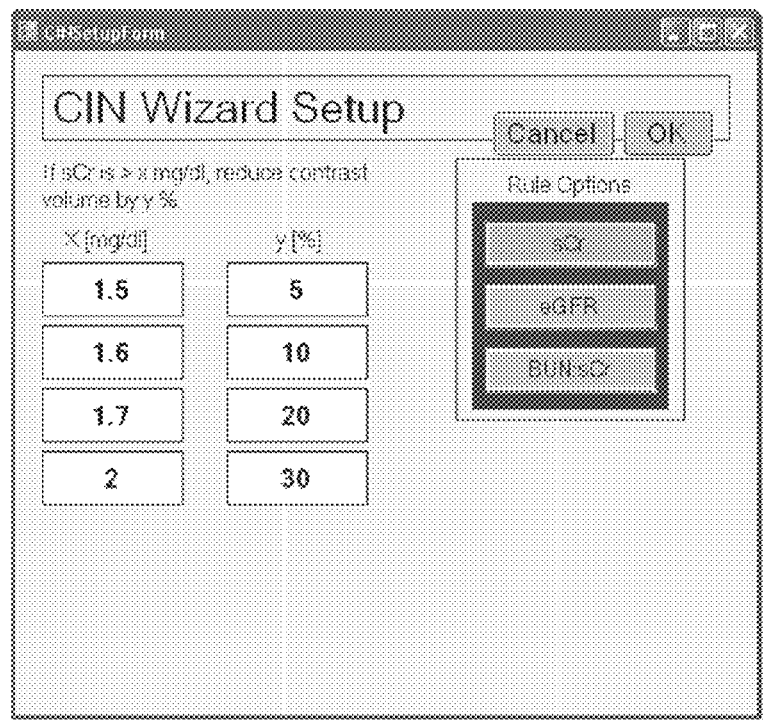
FIG. 9A illustrates an embodiment of a display screen for configuration of Iodine mass reduction as a function of entered serum Creatinine (sCR).
Figure 9B:
FIG. 9B illustrates an embodiment of a keypad entry screen for entry of the patient's sCR wherein the sCR information could be obtained from the lab, a Point of Care Device, from the patient's medical record or can be automatically populated.
Figure 9C:
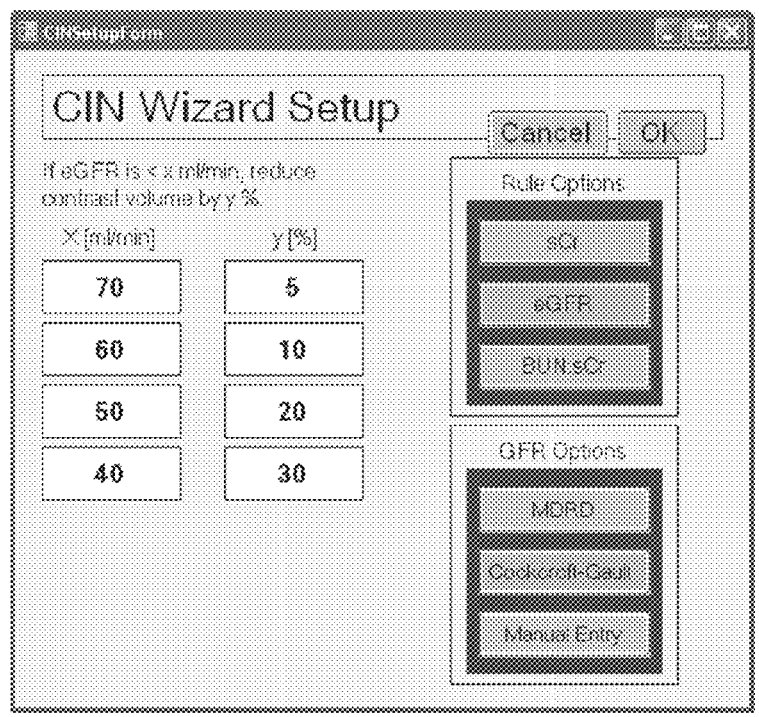
FIG. 9C illustrates an embodiment of a display screen for configuration of iodine mass reduction as a function of estimated Glomerular Filtration Rate (eGFR).
Figure 9D:
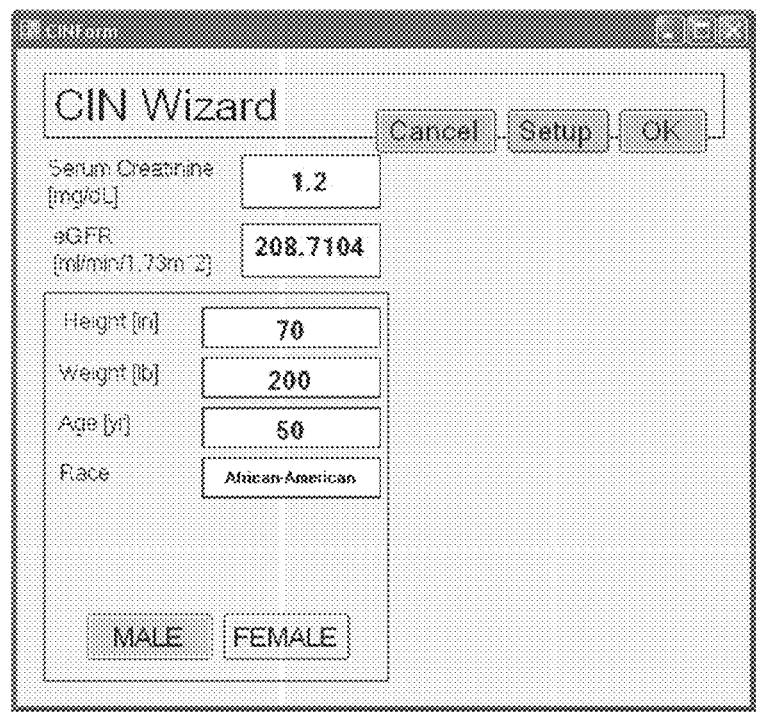
FIG. 9D illustrates an embodiment of a display screen for a clinician wizard for entering per-patient information to compute eGFR using the modification of diet in renal disease or MDRD method.
Figure 9E:
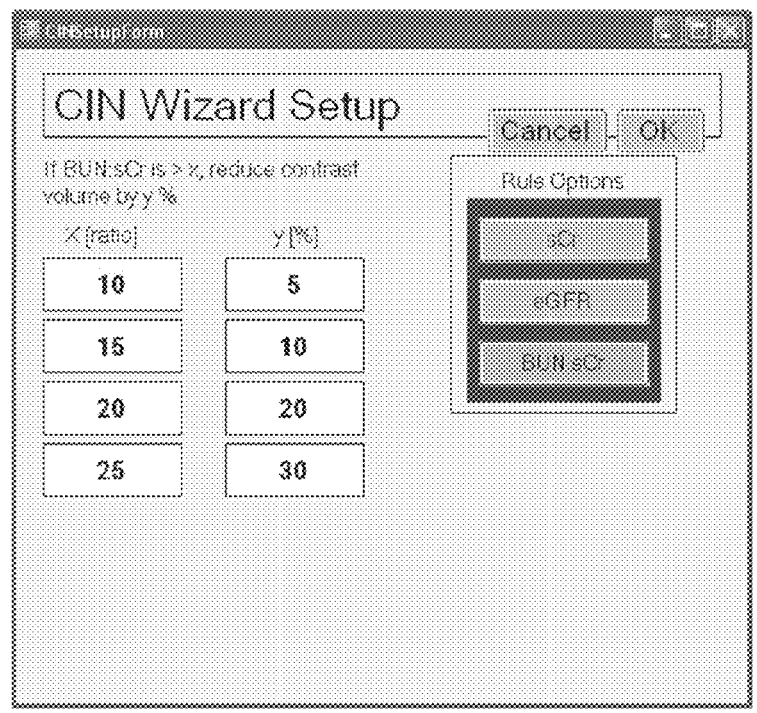
FIG. 9E illustrates an embodiment of a display screen for configuration of iodine mass reduction as a function of entered serum Blood Urea Nitrogen to sCR ratio.
Figure 9F:
FIG. 9F illustrates an embodiment of a display screen in an example wherein the BUN/sCR option is configured.

FIGS. 8A and 8B illustrated a flow chart of one embodiment of per-patient entry of data and computation in one embodiment of a CIN risk assessment algorithm of the present invention. FIGS. 9A through 9G illustrate representative embodiments of display screen for entry of data and computation of an injection protocol via a CIN Wizard Setup routine. FIG. 9A illustrates configuration of iodine mass reduction as a function of entered serum creatinine (sCr). FIG. 9B illustrates and embodiment of a keypad entry for the patient's sCR. The sCR information could, for example, be obtained from the lab, from a Point of Care Device, or from the patient's medical record. This data can also be automatically populated, as described above. FIG. 9C illustrates configuration of iodine mass reduction as a function of estimated Glomerular Filtration Rate (eGFR). The illustrated embodiment allows the clinician to choose one of several methods to compute eGFR–MDRD formulae, the Cockcroft-Gault formula, or manual entry of eGFR. FIG. 9D illustrates an embodiment of a display/data entry screen for entering per-patient information to compute eGFR using the MDRD method. These data can be entered prior to programming injector system 410. FIG. 9E illustrates configuration of iodine mass reduction as a function of entered serum blood urea nitrogen (BUN) to sCR ratio. FIG. 9F illustrates an embodiment of a display screen in the case that the BUN/sCR option was configured. The clinician enters the patient's sCR and BUN. Once again, these data could be populated automatically (for example, via an electronic data connection).

FIG. 9G illustrates an embodiment of a screen display of the CIN Wizard alerting the user of an iodine reduction action taken because the entered/determined renal function parameter (in this example, sCR) exceeded a configured threshold. A sCR of 1.65 mg/dL was entered. The system was configured such that if sCR is greater than 1.6 mg/dL, reduce the contrast volume (iodine) by 10% (see FIGS. 8B and 9A). A contrast protocol was programmed into the injector with 120 ml of contrast in the "A" phase. When the user selected "Protocol Lock", a pre-arm step, the CIN wizard alerted the user of the sCR threshold event and reduced the contrast in the A phase by 10% to 108 ml. There is a similar operation if the eGFR or BUN/sCR options are chosen.

Another technique to minimize the risk and incidence of CIN is to take measures to reduce the amount of contrast agent used during the imaging procedure. These methods include reducing blood flow, image analysis, and imaging control, or combinations thereof. All of these methods may depend on manual or automatic synchronization between the contrast injection system, such as dispensing device 250 in FIG. 2 or injector system 400 in FIG. 6, and the imaging system, such as imaging device 210 in FIG. 2 and imaging system 470 in FIG. 6. In a first example, blood flow may be reduced or occluded in a vessel, vessel tree, or region to be imaged so that contrast or imaging agent is retained locally within the region in a concentrated manner, and is not mixed or diluted with blood as quickly over time. This local concentration allows the region to be imaged using a less diluted amount of contrast, providing greater contrast enhancement (radio-opacity) for a longer period of time. For example, a diagnostic catheter could be constructed that consists of an occluding or flow restricting portion, such as a balloon and an injection lumen, so that contrast may be injected out of the tip of the catheter. Prior to and during the injection, the occluding device proximal to the injection is activated, and the blood flow is reduced as the contrast agent is injected. The reduced blood flow allows the contrast to fill and enhance the vessel distal to the occlusion or flow reduction and provide greater enhancement for a longer time period. Based on this technique, a reduced amount of contrast agent may be used to obtain a diagnostic image. In another embodiment, rather than a balloon, any expandable membrane or structure that temporarily limits flow within the vessel may be used. In addition, the timing of the occlusion and injection may be automated and/or synchronized so that the operation is transparent to the operator and no additional steps are required.

A less invasive technique to reduce the amount of contrast agent injected uses image analysis techniques to allow for a minimal amount of contrast to be used. These methods include road-mapping that uses a maximum or peak image intensity hold or capture, image contrast enhancement, and dynamic subtraction techniques. Such a road-mapping system captures and holds the moments of peak enhancement and subtracts an un-enhanced image taken prior to the contrast agent injection. This technique allows for the non-enhanced structures to be subtracted from the image, and only the peak enhancement to be displayed. For all of these methods, the image analysis may be automated and/or synchronized with the injection so that the operation is transparent to the operator and no additional steps are required. For road mapping, the imaging system may be used to capture and hold the maximum contrast for a given pixel in the image. The pixels will move so that the vessel is "painted" by the slug of contrast as it is injected through, so that the entire vessel does not need to be filled at one time with the contrast agent. In addition, image stabilization techniques, as are common with hand held video cameras may be combined with the maximum intensity hold approach to help minimize artifacts due to organ and patient motion. The image capture and hold may be synchronized with the start of the injection, or synchronized with changes in image intensity in the region of interest or image intensity in vessels that are above some pre-determined threshold.

Image contrast enhancement techniques may also be used to help make lower levels of contrast agent more visible. For example, methods such as histogram equalization, adaptive histogram equalization, de-correlation stretching, or simple adaptive threshold adjustment such as top-hat filtering, or other image based filtering may be used to increase image contrast. In addition, dynamic subtraction techniques may be used to improve the dynamic range of the imaging, allowing for reduced use of contrast agent. For example, the image itself may be used as a template to show temporal increases in contrast over time which can be highlighted, rather than just the image contrast after filling. With this approach, the time-of-flight correlation of the enhancement is what is displayed. For all of these methods, the image enhancement may be synchronized with the start of the injection, or synchronized with changes in image intensity in the region of interest or image intensity in vessels that are above some pre-determined threshold.

Another technique to reduce the amount of contrast agent injected involves imaging control. For example, the intensity of the X-Ray source may be varied to match the concentration of the contrast agent used. For example, for higher concentrations of contrast agent, lower X-Ray intensity may be used. For lower concentrations of contrast agent, greater X-Ray intensity may be used. In the present invention, reduction of X-Ray intensity can be incorporated into the imaging protocol generation algorithm. Also, multiple energy X-Ray source imaging may be used to increase the sensitivity to iodine based contrast agents. Dual X-Ray energy sources with energies selected to use K-edge X-Ray absorption effects may be used to separate calcium and iodine absorption within the image. By switching X-Ray energy during imaging, image subtraction techniques may be used to enhance iodine contrast, allowing the use of lower amounts of imaging contrast agent or lower concentrations. In addition, this technique enhances removal of image artifacts from bone which are primarily composed of calcium. Further, the calcium may be also selectively enhanced, which may be advantageous for detecting calcium deposits in the cardiovascular system. The imaging system X-Ray intensity and selected source timing may be manually or automatically synchronized with the injection system. In addition, the imaging system settings for X-Ray source intensity may be set as a function of injection and patient parameters, including, but not limited to flow rate, volume, flow profile, patient weight, predicted vessel size, predicted vascular tree volume and/or size, and predicted or measured vessel blood flow rate.

As noted previously the standard of medical care to prevent as well as to treat CIN is "hydration therapy". Hydration therapy techniques for treatment of CIN are known from United States Patent Application Publication Nos. 2006/0270971 and 2006/0253064 both to Gelfand et al. and which are incorporated herein by reference. The hydration delivery amount may be determined by a physician or other means, such as a standard or guideline. However, in accordance with this disclosure, the CIN risk assessment algorithm or program described previously within the context of FIGS. 2-3 may include a feature such that the clinician or operator is alerted to the need for patient hydration and/or recommend a new delivery scheme (amount/volume) or adjust the hydration injection parameters, such as total dose or dilution, to reduce the potential risk of CIN. In addition, the systems 200 and 300 of FIGS. 2-3 (and, additionally, the system 400 of FIG. 6) may include features to track the additional cumulative dose/hydration delivered to the patent at the time of imaging, and factor in previous dose history information to provide feedback to the clinician, or end contrast/hydration delivery when a given cumulative dose history limit has been exceeded. Additional information that may be useful includes historical and current clearance rates and renal output, if available. The particular hydration protocol for a patient will depend on specific patient characteristics such as age, weight, gender, and physiological measurements such as cardiac output, BP, creatinine level, renal output. Typical hydration fluids include saline, sodium bicarbonate, and fenoldopam.

Systems 200 and 300 of FIGS. 2-3 (and, additionally, the system 400 of FIG. 6) desirably include the capability to provide or prescribe the hydration in a level dependent on the contrast load given, provide a ratio of hydration in relationship to the contrast load, imaging procedures, and or duration and timing of the procedure. Delivery can be accomplished by a catheter system, IV line or similar methods, in either separate line/catheters or through a common contrast and or saline catheter(s). An automated or controlled hydration delivery system was disclosed previously in connection with FIG. 6 wherein one or more control devices 480 are shown associated with one or more infusion pumps 490. A hydration delivery system in accordance with this disclosure is desirably capable of controlling the delivery of contrast and saline from a combined system, such as the combined system 400 of FIG. 6, or controlling independent injection systems. Separate catheters are desirably provided to access the arterial circulation of the patient and the venous circulation of the system so that contrast and hydration fluids may be supplied independently, in a sequential or simultaneously manner. Catheter(s) could also be positioned to deliver hydration liquid directly to the renal blood supply.

It is known in the medical field to employ a method for protecting a kidney by at least partially occluding at least one renal vein of a patient to reduce the blood flow to a kidney which concurrently increases the venous pressure of the renal vein. This methodology is described in United States Patent Application Publication No. 2004/0167415 to Gelfand et al. which is incorporated herein by reference for the disclosure relating to occlusion of a renal vein. It is further known in the medical field to prevent or mitigate contrast induced nephropathy effect by employing a by pass device which collects contrast-laden blood from the coronary sinus after contrast injection therein, and directs this blood to filtration apparatus. The filtration apparatus filters out the contrast solution and the filtered blood is returned to the patient's body. Such a methodology is described in U.S. Pat. No. 6,554,819 to Reich, the disclosure of which is incorporated herein by reference. Similar methodologies and additional apparatus for carrying out a collection and filtration methodology as described in the Reich patent are also known from the following United States documents, all incorporated herein in their entirety: U.S. Pat. No. 7,363,072 to Movahead which employs and occluding balloon catheter in the coronary vasculature; U.S. Pat. No. 7,163,520 to Bernard et al. which likewise includes the use of an occluding balloon catheter which further removal of contrast-laden blood to an external filtration apparatus; United States Patent Application Publication No. 2005/0256441 to Lotan et al. which includes the use of an occluding balloon catheter with a blood draining or removal capability; and United States Patent Application Publication No. 2006/0013772 to LeWinter et al. It is noted that the Gelfand publication referenced above does not provide for contrast removal from the blood entering the kidneys at the renal artery take-off point.

While methods are known, as evidenced by the foregoing documents, to prevent contrast media from reaching the kidneys such devices concentrate on removal of contrast media immediately downstream from the region of interest, typically at the coronary injection location (e.g., coronary sinus). These documents are not concerned with removal of the contrast media from the bloodstream or by neutralization in the bloodstream. Removal of contrast media may employ, in accordance with this disclosure, various means to extract the media from the bloodstream before it can reach the kidneys. These means differ in the location of removal as well as the method of removal. The location for contrast removal could be at any suitable point of the vasculature downstream of the region of interest of the imaging procedure up to directly proximal of the renal artery take-off within the abdominal aorta. Depending on the region of interest for a venous injection of contrast the removal process could occur in the right atrium or again at a location in the abdominal aorta before the renal artery take-off point.

Figures 10A, 10B:
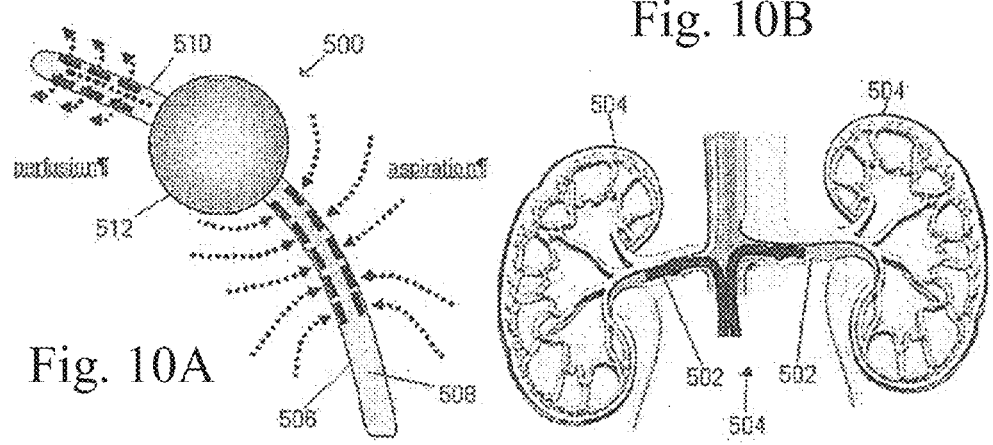
FIG. 10A illustrates an example of contrast removal apparatus of the present invention which removes contrast from the bloodstream via, for example, absorption, adsorption, and/or filtration.
FIG. 10B illustrates the contrast removal apparatus of FIG. 10A inserted into the renal arterial take-off for each kidney in human patient.

Referring to FIGS. 10A-10B, an exemplary contrast removal apparatus 500 in accordance with this disclosure is shown and which employs any of the following methods to remove contrast from the bloodstream: absorption, adsorption, and filtration. All three methods may be achieved either with devices placed intravascularly or extracorporeal. The intravascular application employs a catheter or catheter delivered device that is coated with suitable chemicals to cause absorption or adsorption of contrast molecules or comprises a filtering system that extracts these molecules. FIG. 10B illustrates contrast removal apparatus 500 inserted into the renal arterial take-off 502 for each kidney 504 in human patient.

In use in an extracorporeal application, contrast removal apparatus 500 comprises an extraction device such as a catheter 506 that is connected to an extraction apparatus, such as a peristaltic pump, that actively aspirates contrast contaminated blood and channels it through a filtration (absorption, adsorption) component before returning the blood to the body. Suitable pump apparatus and filtration apparatus may be selected from the United States patents and publications incorporated by reference hereinabove. The aspiration catheter 506 may be placed proximal to the renal arteries, as illustrated, in the abdominal aorta, or in a special adaptation in one or both renal arteries simultaneously or alternately. The aspiration catheter 506 incorporates an aspiration lumen 508 and a perfusion lumen 510. The selectively placed aspiration catheter 506 can incorporate a third lumen (not shown) that allows inflation of an occlusion balloon 512 to isolate the renal blood flow. Such a third or inflation lumen is well-known in the catheter field.

As an alternative to the physical removal of contrast-containing blood and filtration thereof, it is further within the scope of this disclosure to neutralize contrast molecules in the bloodstream without removal physical removal of blood from the patient's body. Such a neutralization technique for blood flowing in the human body is disclosed generally in U.S. patent application Ser. No. 11/469,054 (published as United States Patent Application Publication No. 2008/0097339), incorporated herein in its entirety. Neutralization is achieved by chemically binding the contrast media molecules or by breaking them into non-pathogenic components. The neutralizing chemical may be exposed to the contrast contaminated blood on a coated device (as in United States Patent Application Publication No. 2008/0097339) that temporarily resides in the vasculature upstream from the kidneys. The coated surface preferentially attracts certain components of contrast molecules leaving non-nephroactive components in the bloodstream. In a further adaptation, the indwelling device eludes the chemicals necessary to break up or bind contrast molecules (again as broadly disclosed in United States Patent Application Publication No. 2008/0097339). Alternatively the mechanism of action can be of a catalytic nature where the treated surface is not depleted but rather triggers a chemical reaction of contrast with a second agent that is administered to the bloodstream. The chemicals can also be directly infused into the bloodstream at a location downstream from the area of interest for the imaging procedure.

While the embodiments of system, devices, and methods described hereinabove may be used to mitigate contrast-induced nephropathy occurring during or post a diagnostic and/or therapeutic procedure, those skilled in the art may make modifications and alterations to these embodiments without departing from the scope and spirit of the invention. Accordingly, the foregoing description is intended to be illustrative rather than restrictive.

What is claimed is:

1. A system comprising:
   a pressurizing mechanism to pressurize a fluid comprising a contrast enhancement agent for delivery to a patient; and
   a control system in operative connection with the pressurizing mechanism, the control system comprising:
      a protocol generation system to generate an initial injection protocol comprising a set of injection parameters defining a total amount of the contrast enhancement agent to be delivered to the patient according to the initial injection protocol; and
      a contrast induced nephropathy risk assessment system to adjust one or more of the injection parameters of the initial injection protocol based at least in part upon a measurement of renal function of the patient and an assessment of a risk of contrast induced nephropathy, wherein the assessment of the risk of contrast induced nephropathy is determined, at least in part, on an analysis of the patient's glomerular filtration rate, and
   wherein adjusting one or more injection parameters of the initial injection protocol comprises determining a recommended maximum amount of the contrast enhancement agent to be delivered to the patient, comparing the recommended maximum amount of the contrast enhancement agent to the total amount of the contrast enhancement agent to be delivered to the patient according to the initial injection protocol, and presenting, on a display screen associated with the system, a reduction factor by which the total amount of the contrast enhancement agent to be delivered to the patient according to the initial injection protocol should be reduced.

2. The system of claim 1, wherein the control system is operative to constrain fluid injection to reduce a likelihood of contrast induced nephropathy.

3. The system of claim 1, comprising:
   an analyzing system to analyze a time enhancement curve resulting from injection of the fluid comprising the contrast enhancement agent to provide the measurement of renal function.

4. The system of claim 3, wherein the analyzing system is in operative connection with the control system such that injection of the fluid into the patient can be controlled to reduce the likelihood of contrast induced nephropathy based, at least in part, on the analysis of the time enhancement curve.

5. The system of claim 1, wherein the control system is operative to control injection of the fluid into the patient to reduce the likelihood of contrast induced nephropathy based, at least in part, on input of patient specific parameters.

6. The system of claim 1, further comprising: an input system for input of patient parameters associated with renal function, the input system being in operative connection with the control system.

7. The system of claim 6, wherein the patient parameters comprise at least one of age, body mass index, sex, serum creatinine level in the blood plasma, and blood urea nitrogen.

8. The system of claim 1, comprising a system to determine a therapy for the patient after delivery of the fluid to the patient if the patient is determined to be at risk of contrast induced nephropathy.

9. The system of claim 8, wherein the therapy comprises a hydration therapy.

10. The system of claim 8, wherein the determination of the therapy is based, at least in part, on analysis of a time enhancement curve resulting from injection of the fluid comprising the contrast enhancement agent to provide the measurement of renal function.

11. The system of claim 1, wherein the control system is in communicative connection with a contrast induced nephropathy therapy system.

12. The system of claim 11, wherein the therapy system comprises a pump for introducing therapeutic fluids.

13. The system of claim 1, wherein adjusting one or more injection parameters further comprises adjusting at least one of a flow rate and an injection duration so that the contrast enhancement agent delivered in the injection does not exceed the recommended maximum amount of the contrast enhancement agent.

14. A method of performing an imaging procedure, the method comprising:
   generating an initial injection protocol on a system, the initial injection protocol comprising a set of injection parameters defining a total amount of a contrast enhancement agent to be delivered to a patient according to the initial injection protocol;
   adjusting one or more injection parameters of the initial injection protocol based at least in part upon a determination of renal function of the patient and an assessment of a risk of contrast induced nephropathy, wherein the assessment of the risk of contrast induced nephropathy is determined, at least in part, on an analysis of the patient's glomerular filtration rate, and wherein adjusting one or more injection parameters of the initial injection protocol comprises determining a recommended maximum amount of the contrast enhancement agent to be delivered to the patient, comparing the recommended maximum amount of the contrast enhancement agent to the total amount of the contrast enhancement agent to be delivered to the patient according to the initial injection protocol, and presenting, on a display screen associated with the system, a reduction factor by which the total amount of the contrast enhancement agent to be delivered to the patient according to the initial injection protocol should be reduced;

generating a revised injection protocol based, at least in part, on the reduction factor and the initial injection protocol;

delivering the contrast enhancement agent to the patient according to the revised injection protocol; and imaging at least a portion of the patient.

15. The method of claim 14, wherein the renal function of the patient is determined, at least in part, based upon at least one patient parameter.

16. The method of claim 15, wherein the patient parameter is at least one of age, body mass index, sex, creatinine level, and blood urea nitrogen.

17. The method of claim 14, wherein the renal function of the patient is determined, at least in part, based upon analysis of a time enhancement curve of the contrast enhancement agent in at least one region of interest of the patient.

18. The method of claim 14, further comprising: determining a therapy for the patient after delivery of the fluid to the patient if the patient is determined to be at risk of contrast induced nephropathy.

19. The method of claim 18, wherein the determination of the therapy is based, at least in part, on analysis of a time enhancement curve resulting from injection of the fluid comprising the contrast enhancement agent to determine a measurement of renal function.

20. The method of claim 18, wherein the therapy comprises at least one of hydration therapy and introduction of at least one nephroprotective agent.

21. The method of claim 14, further comprising: determining a therapy for the patient before delivery of the fluid to the patient if the patient is determined to be at risk of contrast induced nephropathy.

22. The method of claim 14, wherein adjusting one or more injection parameters further comprises adjusting at least one of a flow rate and an injection duration so that the contrast enhancement agent delivered in the injection does not exceed the recommended maximum amount of the contrast enhancement agent.

* * * * *